(12) United States Patent
Ueno et al.

(10) Patent No.: US 8,609,826 B2
(45) Date of Patent: Dec. 17, 2013

(54) RNA-SELECTIVE HYBRIDIZATION REAGENT AND USE OF THE SAME

(75) Inventors: Yoshihito Ueno, Gifu (JP); Yukio Kitade, Gifu (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 312 days.

(21) Appl. No.: 12/921,909

(22) PCT Filed: Mar. 11, 2009

(86) PCT No.: PCT/JP2009/054675
§ 371 (c)(1),
(2), (4) Date: Oct. 20, 2010

(87) PCT Pub. No.: WO2009/113580
PCT Pub. Date: Sep. 17, 2009

(65) Prior Publication Data
US 2011/0033863 A1 Feb. 10, 2011

(30) Foreign Application Priority Data

Mar. 11, 2008 (JP) ................................ 2008-061751

(51) Int. Cl.
*C07H 21/00* (2006.01)
*C12Q 1/68* (2006.01)
(52) U.S. Cl.
USPC .......................................... 536/23.1; 435/6.1
(58) Field of Classification Search
USPC .......................................... 536/23.1; 435/6.1
See application file for complete search history.

(56) References Cited

U.S. PATENT DOCUMENTS 7,629,447 B2 12/2009 Kitade et al.

OTHER PUBLICATIONS

Harris et al., "Syntheses of 8-Aminoimidazo [4',5':5,6]pyrido[2,3-d]pyrimidines: Linear Tricyclic Analogs of Adenine," Journal of Heterocyclic Chemistry, Mar.-Apr. 1996, pp. 319-322, vol. 33.
Nielsen et al., "Sequence-Selective Recognition of DNA by Strand Displacement with a Thymine-Substituted Polyamide," Science, 1991, pp. 1497-1500, vol. 254.
Obika et al., "Stability and structural features of the duplexes containing nucleoside analogues with a fixed N-type conformation, 2'-O,4"-C-methyleneribonucleosides," Tetrahedron Letters, 1998, pp. 5401-5404, vol. 39.
Schneider et al., "Oligonucleotides Containing Flexible Nucleoside Analogues," Journal of American Chemical Society, 1990, pp. 453-455, vol. 112.
Augustyns et al., "Influence of the incorporation of (S)-9-(3,4-dihydroxy-butyl)adenine on the enzymatic stability and base-pairing properties of oligodeoxynucleotides," Nucleic Acids Research, 1991, pp. 2587-2593, vol. 19—No. 10.
Azymah et al., "Isotactic Glycero Oligothymidlate. A Convenient Preparation of (R) and (S) 1',2'-Seco 2"-Nor Thymidine," Nucleosides and Nucleotides, 1992, pp. 1241-1255, vol. 11—No. 6.
Nielsen et al., "Incorporation of (R)- and (S)-3',4'-seco-thymidine into oligodeoxynucleotides: hybridization properties and enzymatic stability," Nucleic Acids Research, 1994, pp. 703-710, vol. 22—No. 5.
Minakawa et al., "New Base Pairing Motifs. The Synthesis and Thermal Stability of Oligodeoxynucleotides Containing Imidazopyridopyrimidine Nucleosides with the Ability to Form Four Hydrogen Bonds," Journal of American Chemical Society, 2003, pp. 9970-9982, vol. 125.
Dvorakova et al., "Fluorescent Analogues of Acyclic Inhibitors of S-Adenosyl-L-Homocysteine Hydrolase," Collection of Czechoslovak Chemical Community, 1988, pp. 1779-1794, vol. 53.
Liu et al., "Size-Expanded Analogues of dG and dC: Synthesis and Pairing Properties in DNA," Journal of Organic Chemistry, 2005, pp. 639-647, vol. 70.
Liu et al., "Toward a New Genetic System with Expanded Dimensions: Size-Expanded Analogues of Deoxyadenosine and Thymidine," Journal of American Chemical Society, 2004, pp. 1102-1109, vol. 126.
Liu et al., "A Four-Base Paired Genetic Helix with Expanded Size," Science, Oct. 31, 2003, pp. 868-870, vol. 302.

Clayton et al., "Synthesis of Pyridine-stretched 2'-Deoxynucleosides," Synlett, 2002, pp. 1483-1486, No. 9.
Zhang et al., "A Simple Glycol Nucleic Acid," Journal of American Chemical Society, 2005, pp. 4174-4175, vol. 127.
International Preliminary Report on Patentability completed on Jan. 22, 2010 issued in International Patent Application No. PCT/JP2009/054675 (with translation).
Written Opinion of the International Searching Authority mailed on Apr. 14, 2009 issued in International Patent Application No. PCT/JP2009/054675 (with partial translation).
Aug. 3, 2012 Chinese Office Action issued in Application No. CN200980108476.4 (with partial translation).
Nov. 13, 2012 Japanese Office Action issued in Japanese Patent Application No. 2010-502852 (with English Translation).

*Primary Examiner* — Jezia Riley

(74) *Attorney, Agent, or Firm* — Oliff & Berridge, PLC

(57) ABSTRACT

Provided is a nucleoside derivative which has a high affinity for RNA. Use is made of a nucleoside derivative represented by either formula (1) or formula (2). (In formulae (1) and (2), Z represents a carbon atom or a nitrogen atom; $R_1$ represents a hydrogen atom or a hydroxyl-protecting group; and $R_2$ represents a hydrogen atom or a phosphodiester group).

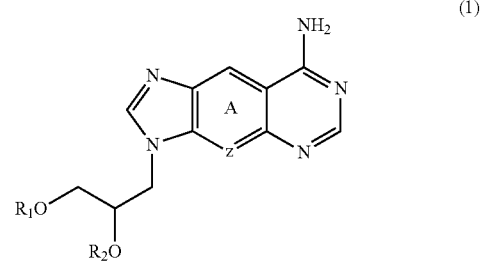

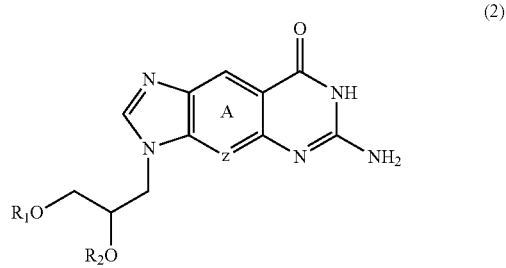

14 Claims, 16 Drawing Sheets

| Base Pair | Tm°C | ΔTm°C |
|---|---|---|
| dA:dT | 52.4 | — |
| F3:dA | 44.1 | -1.5 |
| F3:dT | 45.6 | (-6.8) |
| F3:dG | 42.0 | -3.6 |
| F3:dC | 42.4 | -3.2 |

Numbers in () mean the numbers compared to natural type and other numbers means the numbers compared to F3:dT.

| Base Pair | Tm°C | ΔTm°C |
|---|---|---|
| dA:rU | 35.6 | — |
| F3:rA | 28.6 | -5.5 |
| F3:rU | 34.1 | (-1.5) |
| F3:rG | 29.6 | -4.5 |
| F3:rC | 31.2 | -2.9 |

Numbers in () mean the numbers compared to natural type and other numbers means the numbers compared to F3:rU.

| Base Pair | Tm°C | ΔTm°C |
|---|---|---|
| F1(ss) | 41.0 | — |
| F1:rA | 45.6 | 4.6 |
| F1:rU | 47.7 | 6.7 |
| F1:rG | 47.3 | 6.7 |
| F1:rC | 48.4 | 7.4 |

Drug Transporter MDR1 (P Glycoprotein)
Gene Polymorphizm : -129T/C, 1236C/T, 2677G/A/T, 3435C/T

*MDR1* genotyping : G2677A or T

RNA
5'-GAC UCA CCU UCC CAG G ACC UUC UAG UUC UUU-3'
                          A
                          U
                                                  probe I 3'-QTGG AAG ATC AAG AAA-5'
     probe II 3'-CTG AGT GGA AGG GTC A-5'
3'-CTG AGT GGA AGG GTC G-5'
3'-CTG AGT GGA AGG GTC C-5'
3'-CTG AGT GGA AGG GTC T-5'

Q

SEQUENCE LISTING

<160> NUMBER OF SEQ ID NOS: 10

<210> SEQ ID NO 1
<211> LENGTH: 19

```
<212> TYPE: DNA
<213> ORGANISM: Artificial
<220> FEATURE:
<223> OTHER INFORMATION: Synthetic Construct
<220> FEATURE:
<221> NAME/KEY: modified_base
<222> LOCATION: (10)..(10)
<223> OTHER INFORMATION: adenosine analog

<400> SEQUENCE: 1
ttctgacttn ttttcagaa                                              19

<210> SEQ ID NO 2
<211> LENGTH: 19
<212> TYPE: DNA
<213> ORGANISM: Artificial
<220> FEATURE:
<223> OTHER INFORMATION: Synthetic Construct
<220> FEATURE:
<221> NAME/KEY: modified_base
<222> LOCATION: (10)..(10)
<223> OTHER INFORMATION: adenosine analog

<400> SEQUENCE: 2
ttctgactan atttcagaa                                              19

<210> SEQ ID NO 3
<211> LENGTH: 17
<212> TYPE: DNA
<213> ORGANISM: Artificial
<220> FEATURE:
<223> OTHER INFORMATION: Synthetic Construct
<220> FEATURE:
<221> NAME/KEY: modified_base
<222> LOCATION: (8)..(8)
<223> OTHER INFORMATION: adenosine analog

<400> SEQUENCE: 3
aaggaaanga ggaaaga                                                17

<210> SEQ ID NO 4
<211> LENGTH: 17
<212> TYPE: DNA
<213> ORGANISM: Artificial
<220> FEATURE:
<223> OTHER INFORMATION: Synthetic Construct
<220> FEATURE:
<221> NAME/KEY: modified_base
<222> LOCATION: (7)..(8)
<223> OTHER INFORMATION: adenosin analog

<400> SEQUENCE: 4
aaggaannga ggaaaga                                                17

<210> SEQ ID NO 5
<211> LENGTH: 17
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(11)
<223> OTHER INFORMATION: n is a, c, g, or t

<400> SEQUENCE: 5
tctttcctcn nttcctt                                                17

<210> SEQ ID NO 6
<211> LENGTH: 17
```

```
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(11)
<223> OTHER INFORMATION: n is a, c, g, or u

<400> SEQUENCE: 6 ucuuccucn nuuccuu                                                    17

<210> SEQ ID NO 7
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: n is a, c, g, or u

<400> SEQUENCE: 7
uucugaaaan aagucagaa                                                 19

<210> SEQ ID NO 8
<211> LENGTH: 31
<212> TYPE: RNA
<213> ORGANISM: Homo sapiens
<220> FEATURE:
<221> NAME/KEY: misc_feature
<222> LOCATION: (16)..(16)
<223> OTHER INFORMATION: n is a, c, g, or u

<400> SEQUENCE: 8
gacucaccuu cccagnaccu ucuaguucuu u                                   31

<210> SEQ ID NO 9
<211> LENGTH: 16
<212> TYPE: DNA
<213> ORGANISM: Artificial
<220> FEATURE:
<223> OTHER INFORMATION: Synthetic Construct
<220> FEATURE:
<221> NAME/KEY: modified_base
<222> LOCATION: (16)..(16)
<223> OTHER INFORMATION: adenosine analog

<400> SEQUENCE: 9
aaagaactag aaggtn                                                    16

<210> SEQ ID NO 10
<211> LENGTH: 16
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is a, c, g, or t

<400> SEQUENCE: 10
nctgggaagg tgagtc                                                    16
```

RNA-SELECTIVE HYBRIDIZATION REAGENT AND USE OF THE SAME

TECHNICAL FIELD

The present teaching relates to a hybridization reagent hybridizing to RNA with high selectivity and use of the same.

BACKGROUND ART

For gene expression products, a variety of analytical methods are known. For instance, methods that use in situ hybridization, fluorescence resonance energy transfer, loss of fluorescence polarization, and the like may be cited. In these various analytical methods, while probes, primers and the like for detecting specific base sequences are used, the characteristics required of the probes or the like are different depending on the purpose of the analysis.

So far, nucleoside derivatives with a variety of modifications or alterations have been developed, in probes or the like for detecting specific base sequences. For instance, peptide nucleic acid (PNA) and bridged nucleic acid (BNA) may be cited. In addition, various open sugar ring-type nucleotide derivatives have been reported (Non-patent References 1 to 7). In addition, ring expansion-type modifications in the bases have also been attempted (Non-patent References 8 and 9).

Non Patent Reference 1: P. E. Nielsen, M. Egholm, R. H. Berg, O. Buchardt, Science, 254, 497 (1991).

Non Patent Reference 2: S. Obika, D. Nanbu, Y. Hari, J. Andoh, K. Morio, T. Doi, T. Imanishi, Tetrahedron Lett., 39, 5401 (1998).

Non Patent Reference 3: K. C. Schneider, S. A. Benner, J. Am. Chem. Soc., 112, 453 (1990).

Non Patent Reference 4: K. Augustyns, A. V. Aerschot, A. V. Schepdael, C. Urbanke, P. Herdewijn, Nucleic Acids Res., 19, 2589 (1991).

Non Patent Reference 5: M. Azymah, C. Chavis, M. Lucas, F. Morvan, J.-L. Imbach, Nucleosides & Nucleotides, 11, 1241 (1992).

Non Patent Reference 6: P. Nielsen, F. Kirpekar, J. Wengel, Nucleic Acids Res., 22, 703 (1994).

Non Patent Reference 7: L. Zang, A. Peritz, E. Meggers, J. Am. Chem. Soc., 127, 4174 (2005).

Non Patent Reference 8: N. Minakawa, N. Kojima, S. Hikishima, T. Sasaki, A. Kiyosue, N. Atsumi, Y. Ueno, A. Matsuda, J. Am. Chem. Soc., 125, 9970 (2003).

Non Patent Reference 9: H. Liu, J. Gao, L. Maynard, Y. D. Saito, E. T. Kool, J. Am. Chem. Soc., 126, 1102 (2004).

DISCLOSURE OF THE INVENTION

From the fact that the first product of gene expression is RNA, which is a transcription product, rather than detecting as DNA by RT-PCR, it is desirable that it is one that hybridizes to RNA with a higher selectivity than DNA. In addition, detecting RNA intracellularly in real-time by hybridizing to RNA is also sought.

A PNA is intended to eliminate the electric charges at phosphate positions to diminish electrostatic repulsion so that a PNA/DNA duplex forms a stronger bond than a DNA/DNA duplex. In addition, a BNA increases the binding affinity for the target DNA or RNA by bridging position 2' and position 4' of the ribose ring which becomes pre-locked in the N conformation. Therefore, both PNA and BNA increase stability with respect to DNA and RNA. That is to say, they display a high affinity for not only RNA but also DNA. In addition, most of the various open sugar ring-type derivatives are known to thermally destabilize hybrids with DNA and RNA significantly. In addition, according to the present inventors, the ring expansion-type nucleotides have been shown to not from a stable hybrid with RNA.

In addition, no hybridization reagent for RNA-targeting with a high base specificity to an extent that allows the detection of SNP to be possible at the gene expression level by having base specificity with respect to RNA has been provided.

Thus, it is an object of the present teaching to provide a nucleoside derivative having high affinity for RNA and a preparation method therefor. In addition, another object of the present teaching is to provide a nucleoside derivative having base identification capability and a preparation method therefor. Another object is to provide an application of such a nucleoside derivative as a hybridization reagent.

Based on the structure comparison of a DNA/RNA duplex and a DNA/RNA duplex, the present inventors verified the influence of an open sugar ring on the stability of the DNA/RNA duplex and the influence on base specificity, examined the results in detail and discovered a nucleotide structure that stabilizes the DNA/RNA duplex and, moreover, has base identification capability, to compete the present teaching. According to the present teaching, the following means are provided.

According to the present teaching, a nucleoside derivative represented by any of the following Formulae (1) and (2) is provided.

[C1]

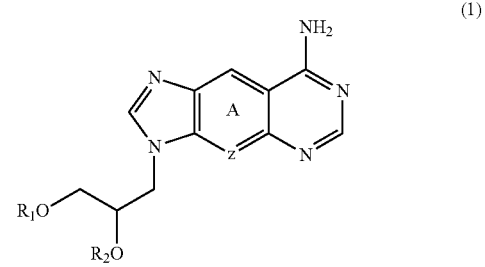

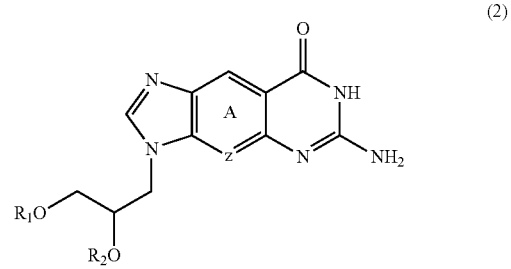

(Where Z represents a carbon atom or a nitrogen atom; $R_1$ represents a hydrogen atom or a hydroxyl-protecting group; and $R_2$ represents a hydrogen atom or a phosphodiester group.)

It is desirable that the nucleoside derivative is represented by the Formula (1) and that the Z is a nitrogen atom.

According to the present teaching, a nucleoside derivative represented by the following Formulae (3) and (4) is provided.

[C2]

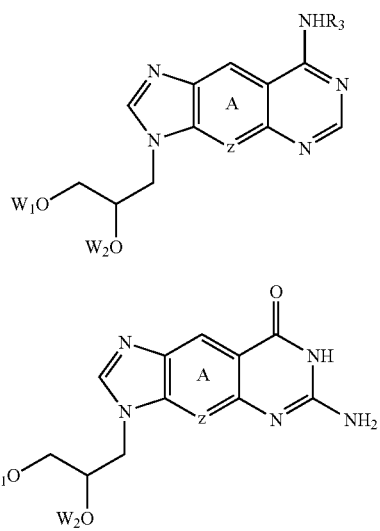

(3)

(4)

(Where Z represents a carbon atom or a nitrogen atom; $W_1$ represents a hydrogen atom or a hydroxyl-protecting group; $W_2$ represents a hydroxyl-protecting group, a phosphoramidite group or a linking group bonding or bonded to a solid phase support; and $R_3$ represents a hydrogen atom or an amino-protecting group.)

According to the present teaching, an oligonucleotide provided with one species or two or more species of nucleotide derivative units represented by any of the following Formulae (5) and (6) is provided.

[C3]

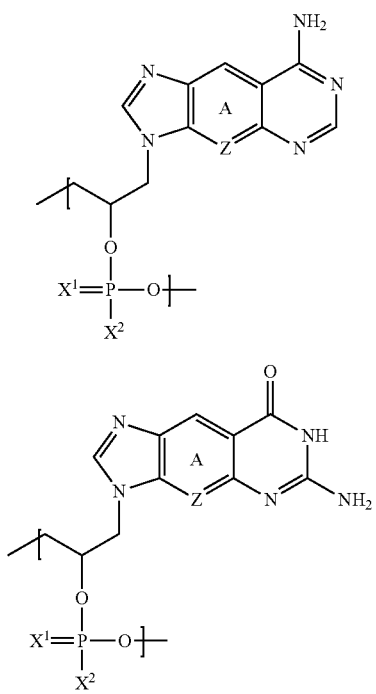

(5)

(6)

(Where Z represents a carbon atom or a nitrogen atom; $X^1$ represents O, S or Se; $X^2$ represents SH (or $S^-$), S or $Se^-$, or an alkyl group having 1 to 4 carbons or a morpholino group.)

According to the present teaching, an RNA hybridization reagent provided with one species or two or more species of nucleotide derivative units represented by any of the Formulae (5) and (6) is provided.

In the hybridization reagent of the present teaching, it is desirable that the nucleotide derivative unit is represented by the Formula (5) and that the Z is a nitrogen atom. In addition, it is also desirable that the nucleotide derivative unit is provided at an extremity. In addition, it is also desirable to have a base sequence capable of forming a stem-loop structure, and provided with the nucleotide derivative unit in the loop.

According to the present teaching, provided is a probe set for detecting a mutation on an RNA, including: a first probe provided with one species or two or more species of nucleotide derivative units represented by any of the Formulae (5) and (6) provided at the 5' end or the 3' end corresponding to a site of the mutation, and one species or two or more species of second probes provided with a deoxynucleotide having a base complementary to a base that has the possibility to be present in a site of the mutation at the 3' end or the 5' end corresponding to the of the mutation.

According to the present teaching, provided is a detection method for a single base polymorphism including the steps of: preparing an RNA sample as a gene expression product having the possibility of containing the single base polymorphism, causing the first probe, the second probe and the RNA sample to contact one another allowing hybridization in combinations of one species or two or more species obtained by combining one species of the first probe and one species of the second probe selected from the probe set of the present teaching; and detecting a fluorescence signal based on the first probe which is a hybridization product among the RNA sample, the first probe and the second probe.

BEST MODE FOR CARRYING OUT THE INVENTION

The present teaching relates to a novel nucleoside derivative represented by any of the following Formulae (1) and (2) and to utilization of the same.

[C4]

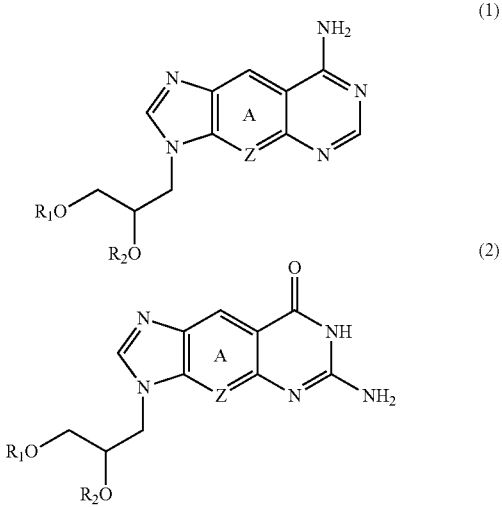

(Where Z represents a carbon atom or a nitrogen atom; $R_1$ represents a hydrogen atom or a hydroxyl-protecting group; and $R_2$ represents a hydrogen atom or a phosphodiester group.)

In order to solve the problems, the present inventors carried out a variety of examinations. As a result of first focusing on the distance between neighboring phosphates in a DNA/DNA duplex and a DNA/RNA duplex and then examining for nucleoside derivatives that allow the inter-phosphate distance to be diminished the duplex thermal stability and the structure thereof, a structure was discovered, in which both thermal stability and base selectivity were compatible.

The present inventors focused on the fact that the inter-phosphate distance (distance between bases) of an RNA/RNA duplex (A-form duplex) was short compared to a DNA/DNA duplex (B-form duplex), and reduced the phosphate spacing in the phosphate backbone from three carbons in a natural nucleoside to two carbons. In addition, in order to increase base selectivity, the present inventors made the nucleobase site to be tricyclic, which is different from a natural nucleoside. According to the nucleoside analog obtained in this way, it was discovered that there was a selectively high affinity for RNA. In addition, it was also revealed that a strong fluorescence centered at 400 nm was emitted. A finding was also obtained, that the gene polymorphism of the gene for the P glycoprotein involved in drug tolerance could be detected by providing a nucleoside provided with such affinity and fluorescence characteristics.

From the fact that the nucleoside derivative of the present teaching has a high RNA selectivity compared to the conventional form, it can be utilized in gene therapy and various study methods with RNA as the target, such as antisense and siRNA methods. In addition, the nucleoside derivative of the present teaching being fluorescent per se, it is extremely advantageous for the detection of gene polymorphism or the like.

Figure 1:
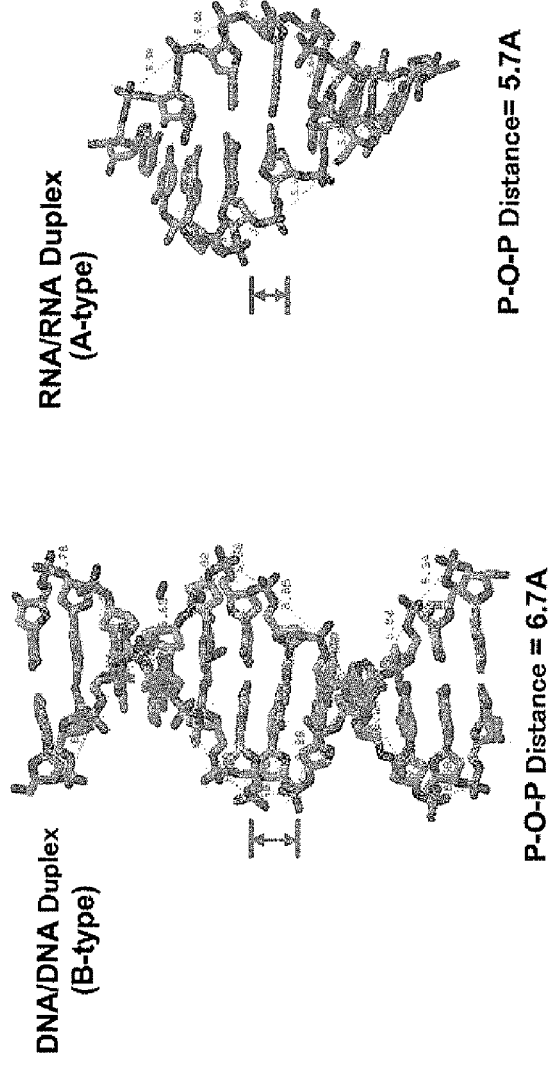
FIG. 1 shows inter-phosphate distances in a DNA/DNA duplex and a DNA/RNA duplex and nucleoside alterations based thereon.
Figure 1:
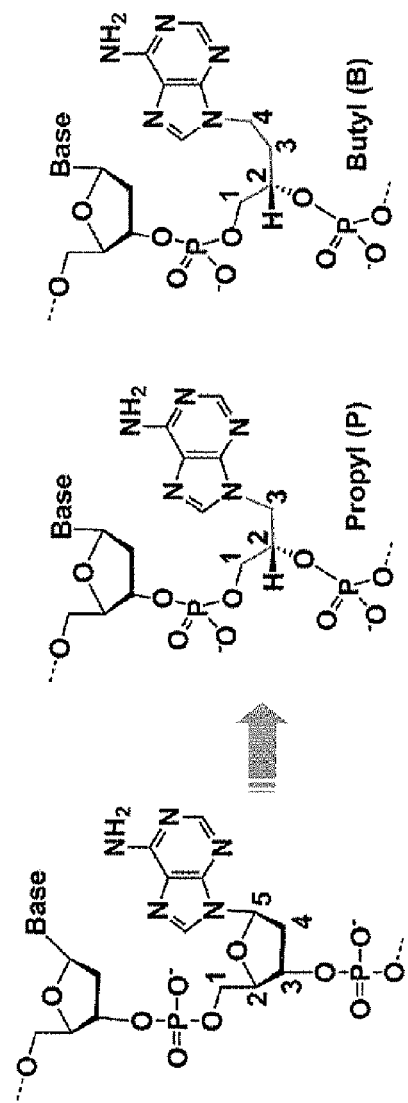
Figure 2:
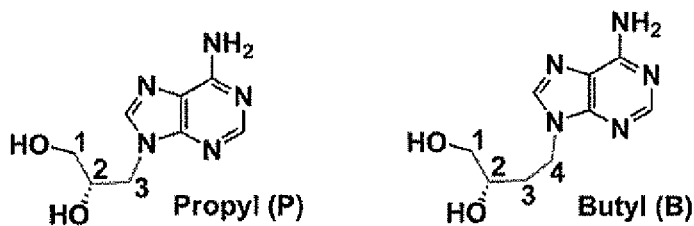
FIG. 2 shows the evaluation results of DNA/DNA duplex thermal stability and base selectivity for primary altered nucleoside derivatives.
Figure 2:
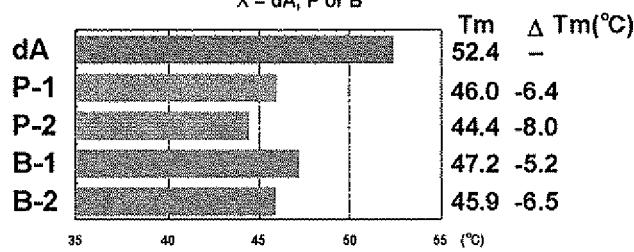
Figure 2:
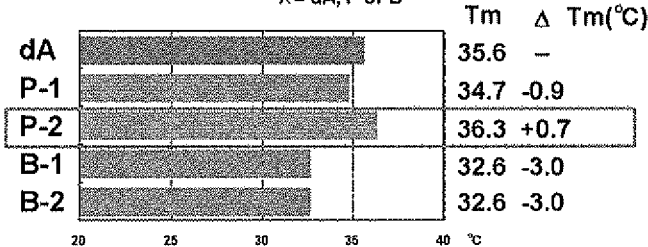
Figure 3:
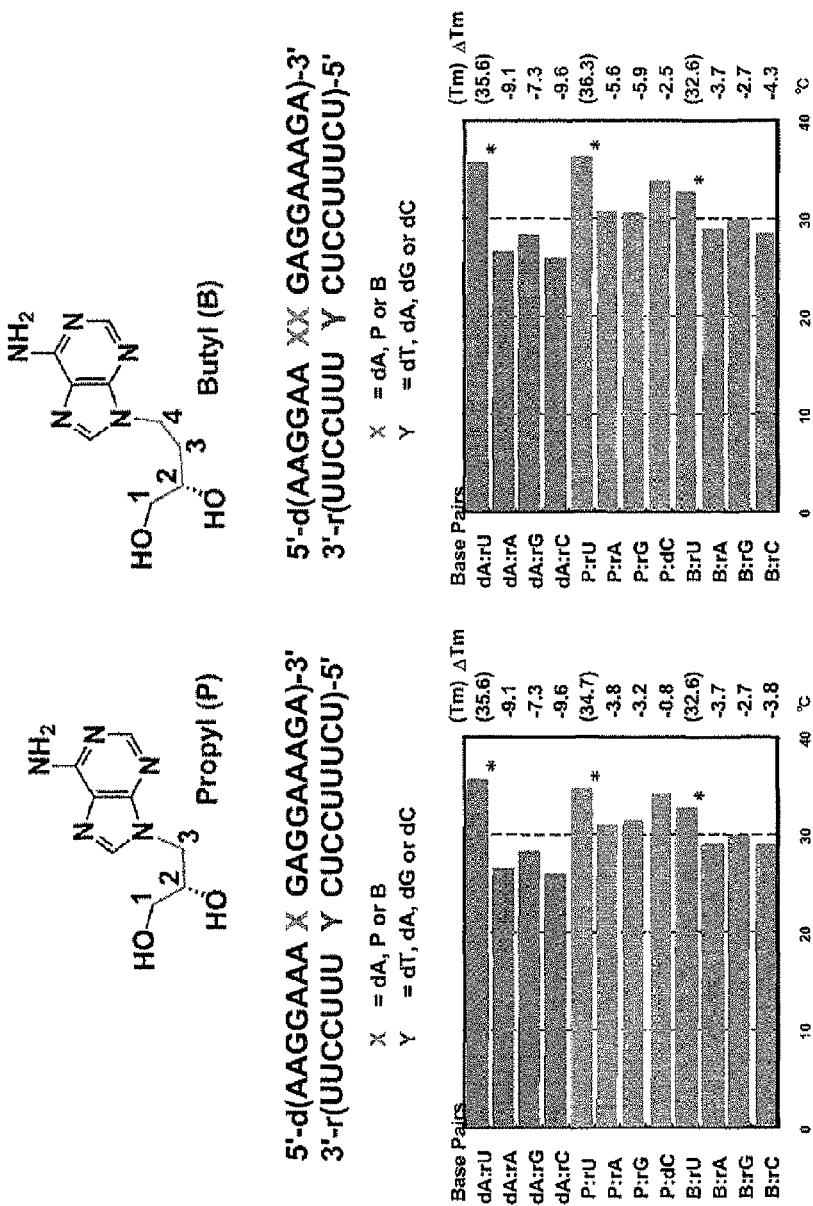
FIG. 3 shows the evaluation results of DNA/RNA duplex thermal stability and base selectivity for the primary altered nucleoside derivatives.
Figure 4:
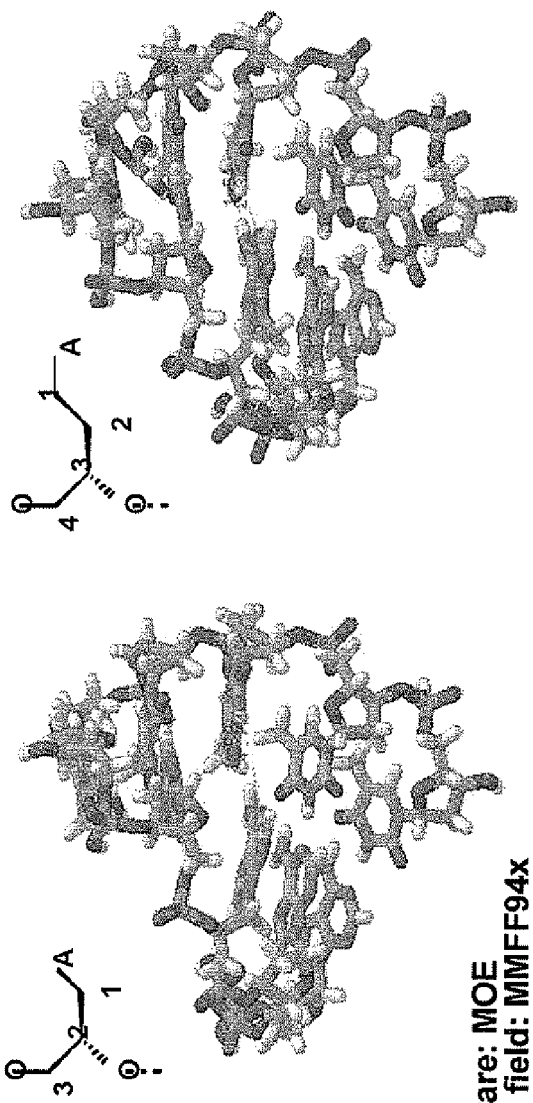
FIG. 4 shows MOE-based modeling results for the primary altered nucleosides.
Figure 5:
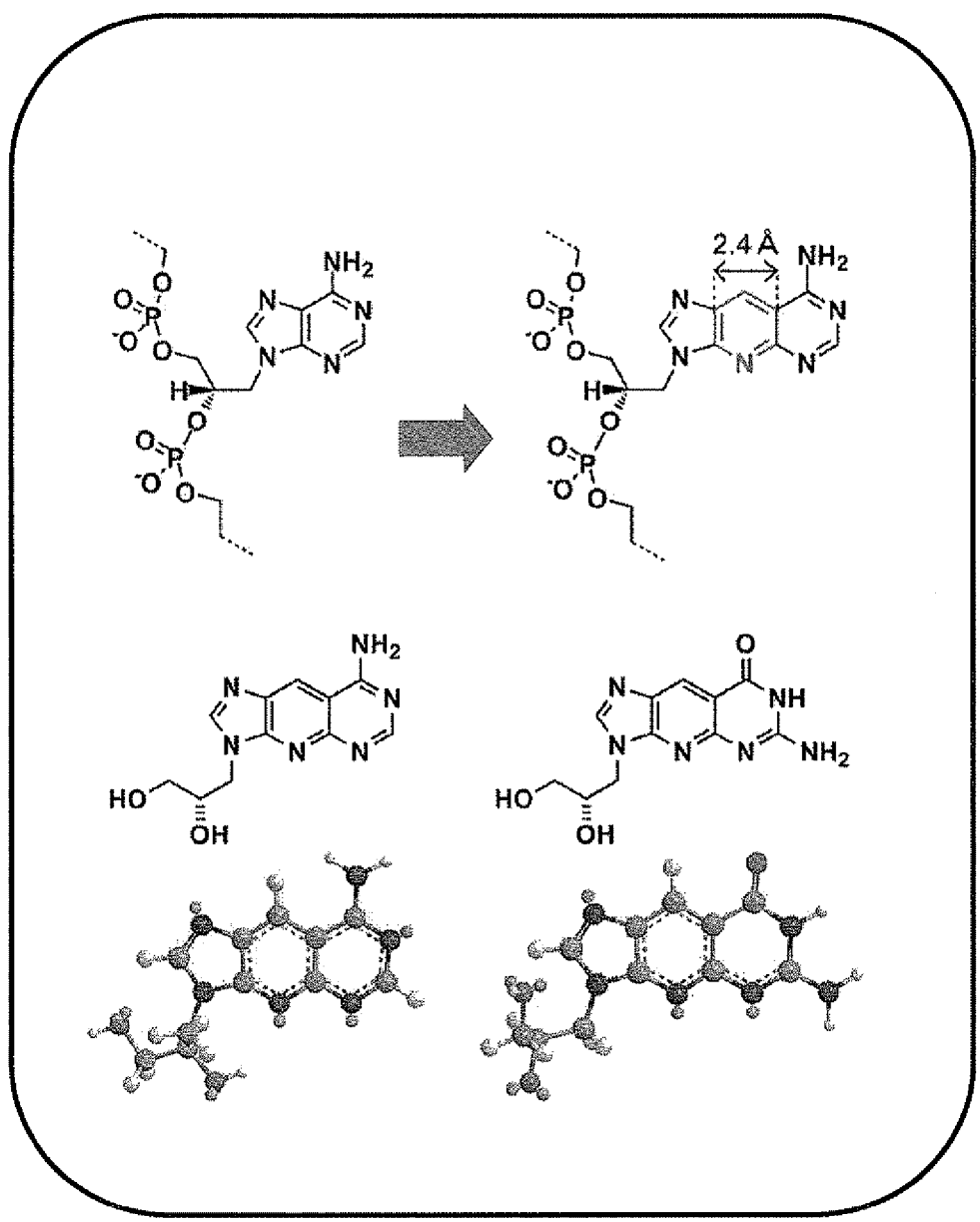
FIG. 5 shows the preparation of secondary altered nucleoside derivatives (the nucleoside derivatives of the present teaching).
Figure 6:
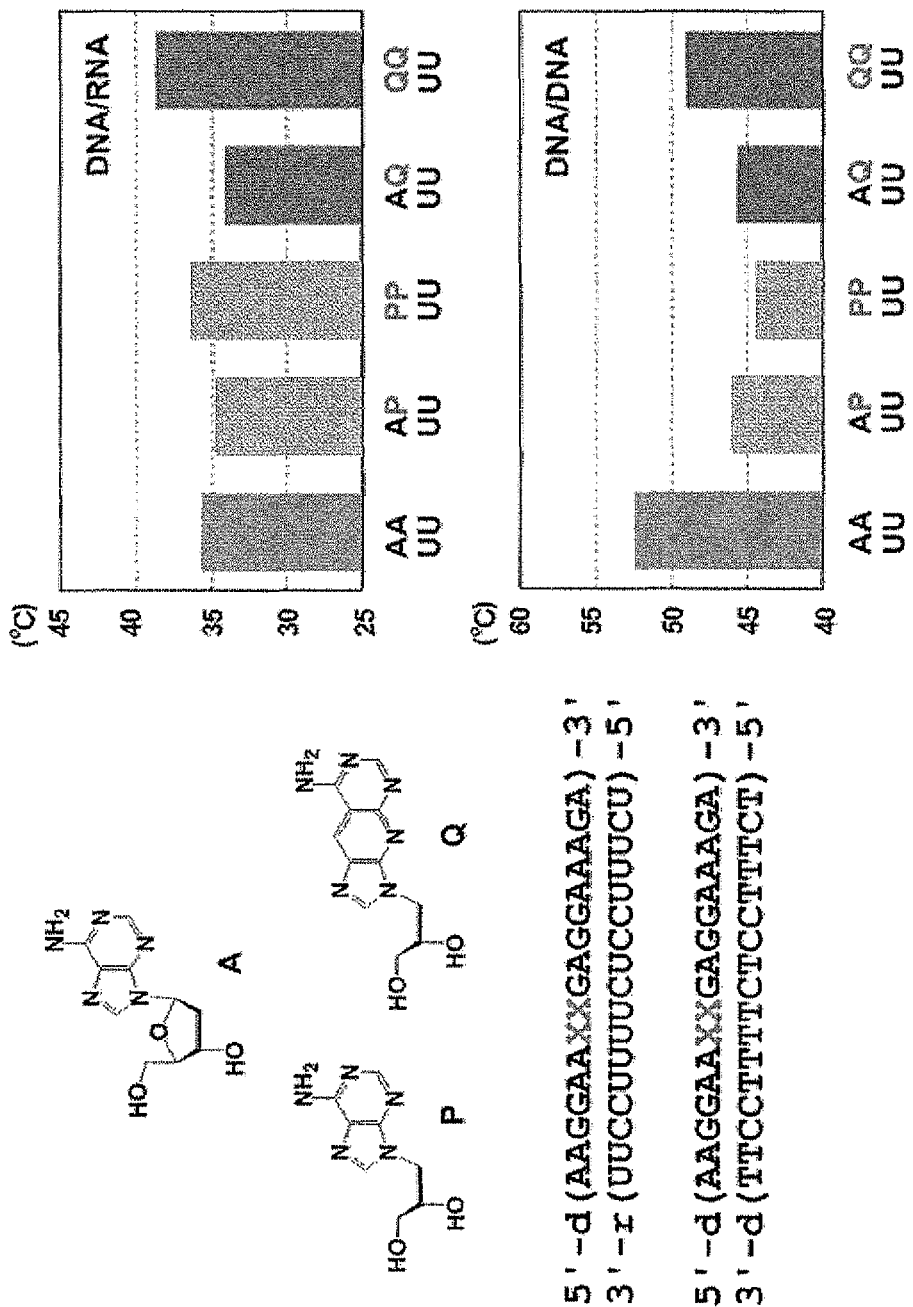
FIG. 6 are graphs showing the thermal stability (Tm values) of DNA/RNA duplexes and DNA/DNA duplexes of oligonucleotides containing the secondary altered nucleoside derivative.
Figure 7:
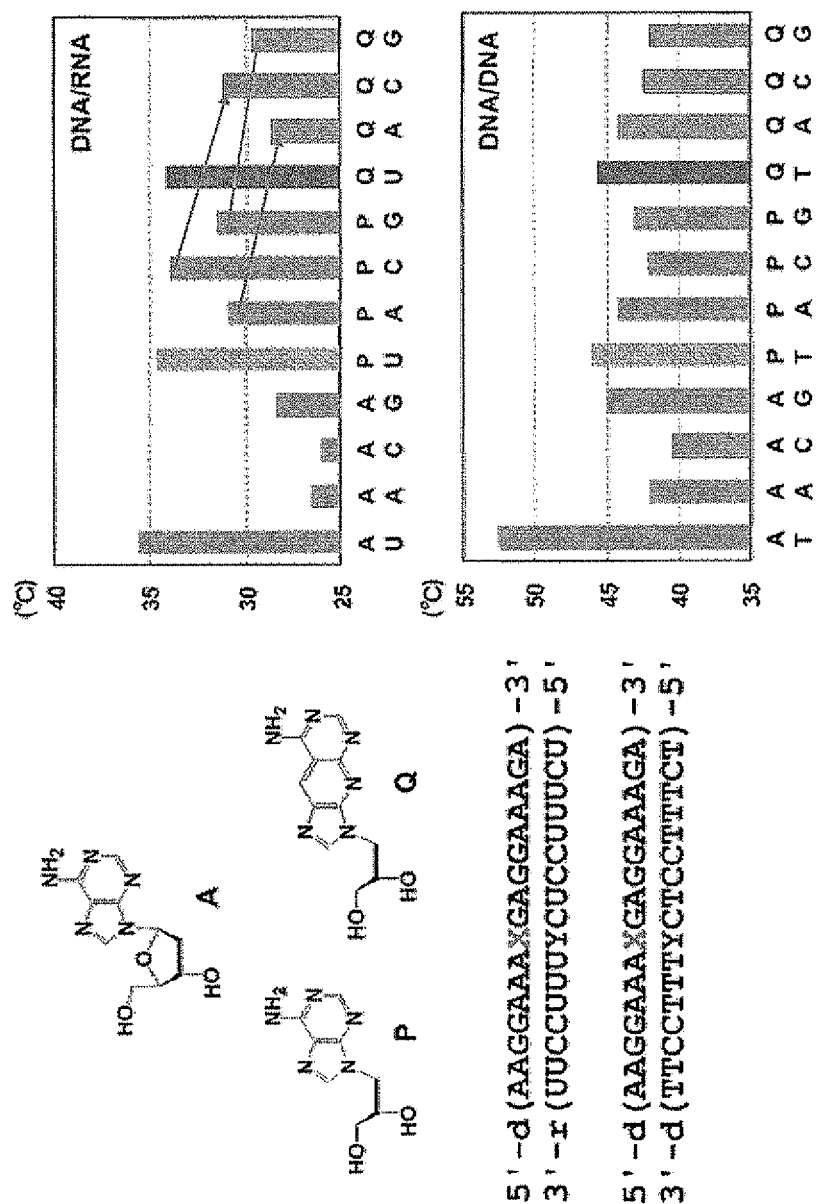
FIG. 7 are graphs showing the base selectivity (Tm values) of the secondary altered nucleoside derivative in DNA/RNA duplexes and DNA/DNA duplexes.
Figure 8:
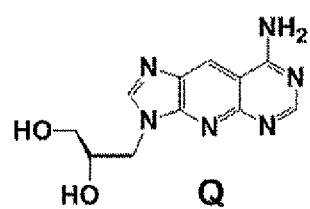
FIG. 8 shows the fluorescence spectrum of the secondary altered nucleoside derivative.
Figure 8:
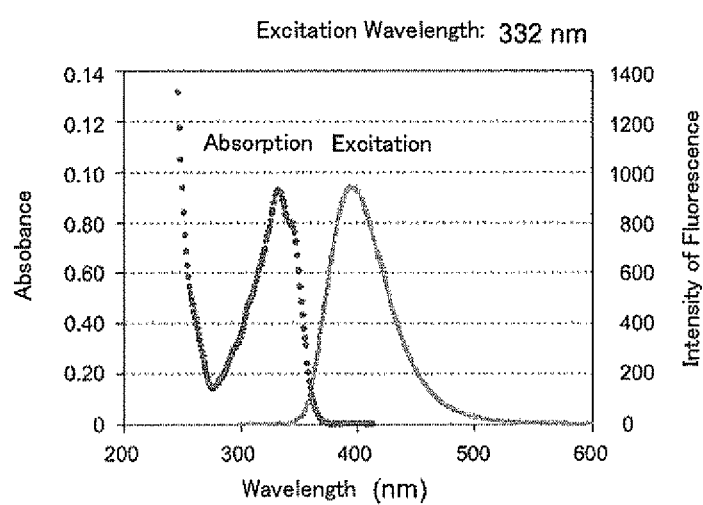

Hereafter, an overview of the present teaching will be described by referring to the figures. FIG. 1 is a figure showing inter-phosphate distances in a DNA/DNA duplex and a DNA/RNA duplex and nucleoside alterations based thereon, FIG. 2 is a figure showing the evaluation results of DNA/DNA duplex thermal stability and base selectivity for primary altered nucleoside derivatives, FIG. 3 is a figure showing the evaluation results of DNA/RNA duplex thermal stability and base selectivity for the altered nucleoside derivatives, FIG. 4 is a figure showing MOE-based modeling results for the altered nucleosides, FIG. 5 is a figure showing the preparation of secondary altered nucleoside derivatives (the nucleoside derivatives of the present teaching). In addition, FIG. 6 is a graph figure showing the thermal stability (Tm values) of DNA/RNA duplexes and DNA/DNA duplexes of oligonucleotides containing the secondary altered nucleoside derivative, FIG. 7 is a graph figure showing the base selectivity (Tm values) of the secondary nucleoside in the DNA/RNA duplexes and the DNA/DNA duplexes, and FIG. 8 is a figure showing the fluorescence spectrum of the secondary altered nucleoside derivative.

Note that MOE is a program based on molecular mechanics methods, and the modeling results of FIG. 4 carried out the program using the force field of MMFF94x.

As shown in FIG. 1, when the averages of inter-phosphate distances was calculated for two types of duplex structures, they were found to be 6.7 Å for the DNA/DNA duplex and 5.7 Å for the DNA/RNA duplex, respectively. That is to say, the inter-phosphate distance in the DNA/RNA duplex was found to be short compared to a DNA/DNA duplex. Thus, the present inventors focused on the difference in inter-phosphate distances, proposed to use as base analogs propyl adenine and butyl adenine in which the neighboring phosphates spacing is two carbons (while it is three carbons in a conventional nucleoside) so as to decrease the inter-phosphate distance (proposition of a primary altered nucleoside derivative), synthesized an oligonucleotide containing this, and verified the RNA selectivity thereof. The verification compared the thermal stabilities of both DNA/DNA and DNA/RNA duplexes via the Tm values while comparing the base selectivities with respect to the four types of bases in an RNA via the Tm values. The results are shown in FIGS. 2 and 3.

As shown in FIG. 2, it was found that while with the butyl-type one both DNA/DNA and DNA/RNA duplexes were thermally destabilized, with the propyl-type, although the duplex with DNA was thermally destabilized, the duplex with RNA was thermally stabilized, albeit slightly. In addition, as shown in FIG. 3, with the altered analogs (middle four bars and bottom four bars in each graph) the base selectivity was found to be low compared to unmodified ones (top four bars in each graph).

Thus, when MOE modelings of DNA/RNA duplexes with these two species of analogs introduced were performed, as shown in FIG. 4, it was found that in contrast to the distances between the atoms involved in hydrogen bonds being within the hydrogen bondable 3 Å with the butyl-type one (FIG. 4 right), they were greater with the propyl-type one (FIG. 4 left), with insufficient lengths to form hydrogen bonds. The present inventors reasoned whether the duplex was thermally destabilized with the butyl-type one due to the flexibility of the side chain being high while the distance to the complementary base was sufficient, and whether base selectivity was decreased with the propyl-type one due to the distance to the complementary base being insufficient while the flexibility of the side chain was lower and the thermal stability was maintained higher than the butyl-type.

Thus, the present inventors designed as secondary nucleoside derivatives the derivatives with a pyridine ring introduced into the base position of the propyl-type analogs in order to maintain the distance to the complementary base, and synthesized amidite compounds for DNA synthesis and oligonucleotides (refer to FIG. 5). As shown in FIG. 5, these are all tricyclic compounds.

As shown in FIG. 6, it was found that the oligonucleotide (DNA) containing the secondary altered nucleoside derivative was destabilized in a duplex with a DNA, while in a duplex with an RNA, when the number of derivatives increased, on the contrary, the thermal stability of the duplex increased. In addition, as shown in FIG. 7, it was found that the oligonucleotide (DNA) containing the secondary altered nucleoside derivative had low selectivity when a DNA was the complementary strand, while when an RNA was the complementary strand, becoming tricyclic increased base selectivity more than the primary altered nucleoside derivative.

In addition, as shown in FIG. 8, the secondary altered nucleoside derivative was shown to have a strong fluorescence centered at 400 nm, allowing a hybridization product to be detected directly by fluorescence.

From the foregoing, it was found that the present teaching could provide a nucleoside derivative having RNA-targeted duplex stability and base discrimination ability oligonucleotide containing this, by providing an open sugar ring structure where a propyl group has been replaced by a deoxyribose so as to reduce the distance between neighboring phosphates in an oligonucleotide, and providing a ring-extended base structure and in order to maintain a distance enabling the formation of hydrogen bonds between complementary bases. In addition, since such altered nucleoside derivatives were revealed to have fluorescence, it was found that they can be conferred a single base discrimination ability.

Hereafter, various embodiments of the present teaching will be described in detail.

Hereafter, nucleoside derivative, oligonucleotide preparation methods therefor and compounds used therein, and applications thereof, which are embodiments of the present teaching, will be described in detail. Note that, conventional techniques of molecular biology and nucleic acid chemistry, which are in the technical scope of a person of ordinary skill in the art, related to the present teaching, are described in the literature. It is possible to refer to, for instance, Sambrook et. al, Molecular Cloning: A Laboratory Manual, Cold Spring Harbor Laboratory, Cold Spring Harbor, N.Y., 1989; Gait, M. J., Oligonucleotide Synthesis, Compilation (1984); Hames, B. D. and Higgins, S. J., Nucleic Acid Hybridization, Compilation (1984); and a series of Methods in Enzymology, Academic Press, Inc.

(Nucleoside Derivative)

The nucleoside derivative of the present teaching is a compound represented by the Formula (1) or the Formula (2). In these compounds, Z represents a carbon atom (CH) or a nitrogen atom.

In addition, the hydrogen atoms bonded to the ring-constituting carbon atoms of the ring A in these compounds may be unsubstituted or may be substituted. Chain alkyl group having 1 to 4 carbons are desirable as substituents. That is to say, a methyl group, an ethyl group, an n-propyl group, an isopropyl group, an n-butyl group, an isobutyl group and a tert-butyl group may be cited. When steric hindrance or the like is considered, there are cases where a methyl group and an ethyl group can be preferably used. In addition, while the number of substituents is also not limited in particular, on the order of one or two is desirable in cases where steric hindrance or the like is a problem.

$R_1$ can be a hydrogen atom or a hydroxyl-protecting group. For the hydroxyl-protecting group, ones that are well known can be used. Concrete examples may be cited, which are the same ones as those described at a later stage. In addition, $R_2$ can be a hydrogen atom or a phosphodiester group ($PO_3$). There is no particular limitation as a phosphodiester group. One species of oxygen atom bonded through a double bond to the phosphorous atom can be replaced to become O, S or Se, and the other hydroxyl group (oxygen ion) can be replaced to become SH (or $S^-$), S or $Se^-$, an alkyl group having 1 to 4 carbons or a morpholino group. As various phosphodiester groups obtained by combining these $X^1$ and $X^2$, for instance, various groups in the following Formula (7) (from which the oxygen atom linked to the carbon atom has been removed) may be cited.

[C5]

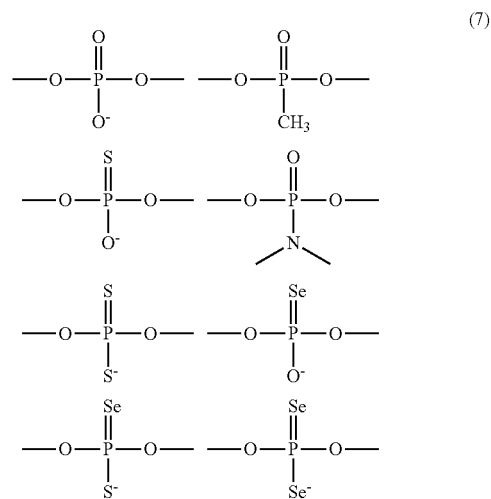

(7)

The nucleoside derivative represented by the Formula (1) can be used as an adenosine analog. In addition, the nucleoside derivative represented by the Formula (2) can be used as a guanosine analog. In addition, when provided at $R_2$ with a phosphodiester bonding group, the nucleoside derivatives represented by the Formulae (1) and (2) become nucleotide derivatives.

In addition the nucleoside derivative of the present teaching can emit fluorescence. That is to say, a fluorescence having a peak near 400 nm can be emitted when light is shone with an excitation wavelength on the order of 330 nm. Therefore, hybridization with a specific RNA, a specific base, or the like can be detected readily.

The present nucleoside derivative can be synthesized by extending the ring in the purine base according to descriptions in P. A. Harris and W. Pendergast, J. Heterocyclic Chem., 33, 319 (1996). For instance, the compound represented by the Formula (1) is synthesized by the following Scheme 1.

[C6]

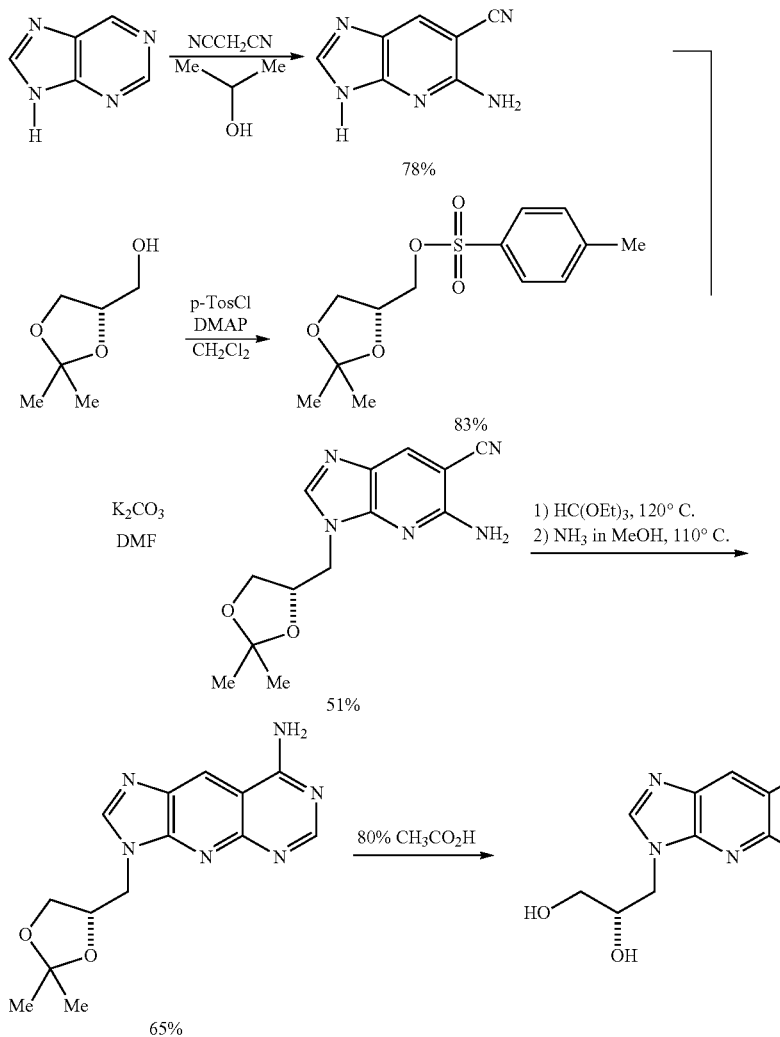

(Nucleoside Derivative Suitable to Oligonucleotide Synthesis)

As nucleoside derivatives that are suitable to oligonucleotide synthesis, the compounds represented by the following Formulae (3) and (4) may be cited. Note that Z and ring A in the Formulae (3) and (4) have the same meanings as Z in the Formulae (1) and (2).

[C7]

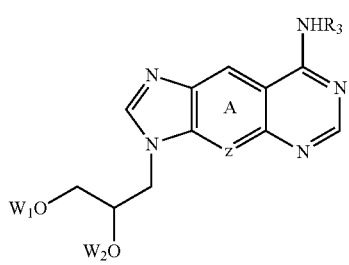

(3)

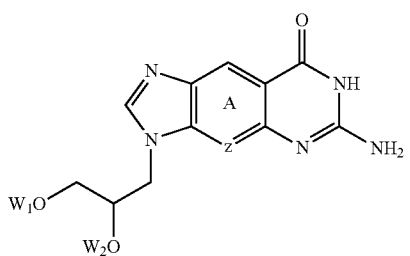

-continued (4)

In the Formulae (3) and (4), $W_1$ can represent a hydrogen atom or a hydroxyl-protecting group. As the hydroxyl-protecting group, it suffices to be a group protecting a hydroxyl group from an unintended reaction. As such hydroxyl-protecting groups, various conventionally well known hydroxyl-protecting groups can be used, with no particular limitation. The preferred protecting group of the present teaching is a fluorenyl methoxycarbonyl group (FMOC group), a dimethoxytrityl group (DMT group), a tert-butyldimethylsilyl group (TBDMS group), a monomethoxytrityl group, a trifluoroacetyl group, a levulinyl group or a silyl group. The preferred protecting group is a trityl group and is selected from, for instance, a dimethoxytrityl (DMT) and a tert-butyldimethylsilyl group (TBDMS group).

In addition, $W_2$ represents a hydroxyl-protecting group, a phosphoramidite group or a linking group bonding or bonded to a solid phase support. Compound in which $W_2$ is a phosphoramidite group (amidite compound) can be to synthesize an oligonucleotide by being used as a phosphoramidite reagent in a phosphoramidite method. Note that in the present teaching, the phosphoramidite group can be represented by the following Formula (8).

[C8]

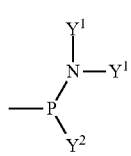

(8)

(in the Formula (8), each $Y^1$ independently may be identical or different, represents a branched or a linear alkyl group having 1 to 5 carbons, and $Y^2$ represents a branched or a linear alkyl group having 1 to 5 carbons or an optionally substituted alkoxyl group.)

In the Formula (8), while $Y^1$ is not limited in particular, the isopropyl group may be cited as desirable, and in addition, —OCH$_3$, —OEtCN, —OCH$_2$CHCH$_2$, and the like may be cited as $Y^2$.

In addition, compounds in which $W_2$ in the Formulae (3) and (4) is a linking group bonding to a solid phase support are retained on the solid phase support by bonding the linking group to a given functional group on the solid phase support such as an amino group. Then, compounds in which $W_2$ in the Formulae (3) and (4) is a linking group bonded to a solid phase support can be used as starting materials for various solid phase nucleic acid synthesis methods, since the nucleoside derivative of the present teaching is bonded to the solid phase support through the linking group. Oligonucleotides having units represented by the Formula (5) or the Formula (6) can be prepared by using this starting material.

Here, as a solid phase support, a general macromolecular support is used and, for instance, CPG (controlled pored glass) or HCP (highly cross-linked polystyrene), a species of gel and the like may be cited. In addition, the solid phase support may have an suitable spacer. The linking group is a linker that links the solid phase support and the present compound. Well known succinic acid ester linker, oxalic acid ester linker, silanediyl linker, silyl linker and the like can be used as such linking groups.

Note that $R_3$ in the Formula (3) can be a hydrogen atom or an amino-protecting group. The primary amino group from the adenine base is protected with a suitable protecting group as necessary. Such protection method and protecting group are well known to a person of ordinary skill in the art. As amino-protecting groups, for instance, a benzoyl group, an acetyl group and a phenoxy acetyl group may be cited.

Such a nucleoside derivative represented by the Formula (3) or the Formula (4) is synthesized from the nucleoside derivative represented by the Formula (1) or the Formula (2) by known methods. For instance, various nucleoside derivatives represented by the Formula (3) are synthesized by the following Scheme 2.

[C9]

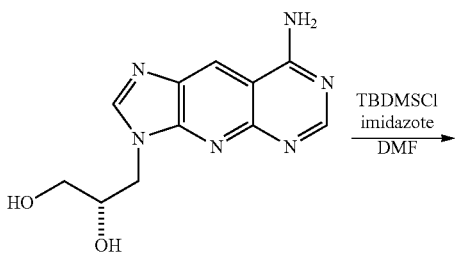

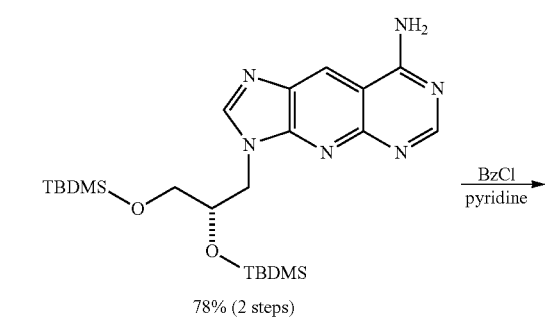

78% (2 steps)

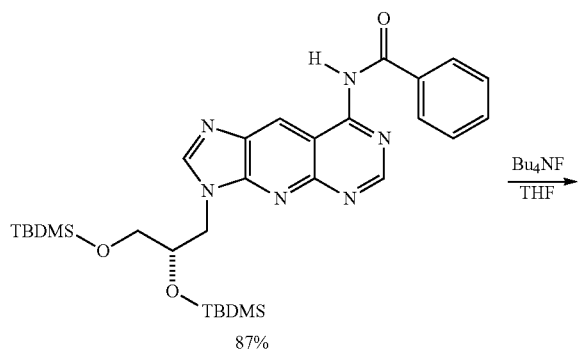

87%

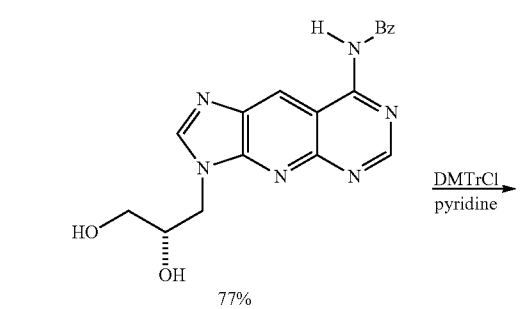

77%

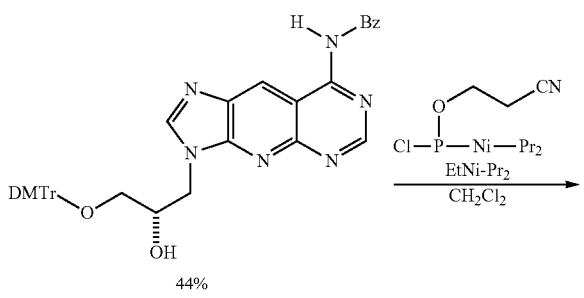

44%

-continued

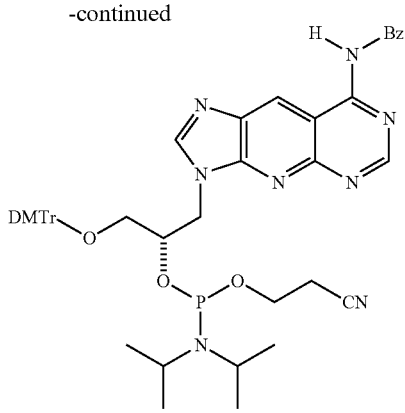

47%

$^{31}$P-NMR (CDCl$_3$): δ 149.1 & 150.2 ppm (Oligonucleotide)

The oligonucleotide of the present teaching can be provided with one species or two or more species of nucleotide derivative units represented by either of the following Formulae (5) and (6). Z in the Formulae (5) and (6) has the same meaning as Z in the Formula (1) or the like, and also regarding the A ring, the meaning is the same as the A ring in the Formula (1) or the like.

[C10]

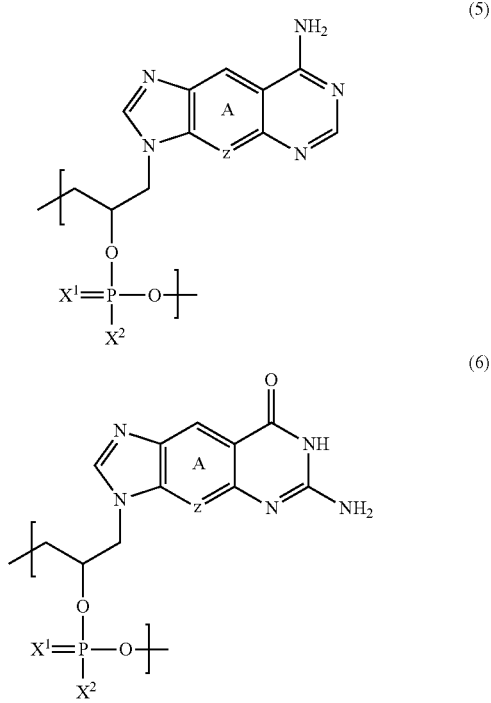

In the Formulae (5) and (6), $X^1$ can be O, S or Se, and $X^2$ can be SH (or S$^-$), S or Se$^-$, an alkyl group having 1 to 4 carbons or a morpholino group. As such a phosphodiester group, various groups described in the Formula (7) may be cited.

In the oligonucleotide of the present teaching, the nucleotide derivative unit may be one species or more, or two species or more. In addition, there may be one or a plurality, and it may constitute the entirety. The nucleotide derivative unit contained in the oligonucleotide of the present teaching is determined according to the oligonucleotide application or the like.

In addition, there is also no particular limitation on the position of the nucleotide derivative unit in the oligonucleotide. It can be provided at the 5' end, at the 3' end and at any parts elsewhere. Note that in the oligonucleotide of the present teaching, at the 5' end, a hydroxyl group may be bonded or a phosphate group (PO$_4$) may be bonded. In addition, similarly, at the 3' end of the oligonucleotide, a hydroxyl group may be bonded or a phosphate group (PO$_4$) may be bonded. Moreover, the 5' end and the 3' end can respectively adopt a suitable structure as necessary.

The oligonucleotide of the present teaching can be provided with a ribonucleotide and/or a deoxyribonucleotide in addition to the nucleotide unit of the present teaching. The oligonucleotide of the present teaching may be an oligonucleotide comprising only deoxyribonucleotides in addition to the nucleotide unit of the present teaching, may be an oligonucleotide comprising only ribonucleotides in addition to the nucleotide unit of the present teaching, and furthermore, may be an oligonucleotide containing both deoxyribonucleotides and ribonucleotides in addition to the nucleotide unit of the present teaching. Since an RNA/DNA duplex and an RNA/RNA duplex both have an A-form duplex structure, the oligonucleotide of the present teaching, which is an RNA, also can stabilize a duplex with a complementarily RNA strand.

An oligonucleotide is to mean a polymer, in which a nucleotide serves as a monomer unit, having a plurality of the monomer units, and the oligonucleotide is deemed to include polymers of nucleotides typically on the order of several or more to 100 or less. While the oligonucleotide of the present teaching can have a length that is suited to an application, when the synthesis of the oligonucleotide is considered, 10 or more and 35 or less is desirable. In addition, in the case of an antisense, it can be on the order of 10 or more and 30 or less; in addition, in the case of an siRNA, the chain length of the total of B and C is preferably 15 or more and 35 or less, and more preferably 30 or less. In the case of a primer, it is 10 or more and 30 or less, in the case of a probe, 10 or more and 30 or less is preferred, and in the case of a molecular beacon, 15 or more and 40 or less is preferred.

Note that according to the present teaching, obviously, a polynucleotide provided with the nucleotide derivative unit of the present teaching is also provided.

In addition, an altered nucleotide other than the nucleotide unit of the present teaching may be provided. An altered nucleotide is to refer to having some sort of chemical modification performed on various portions of the nucleotide, that is to say, the base, the sugar portion and the phosphoester portion.

The oligonucleotide of the present teaching can be synthesized by conventionally well known nucleic acid synthesis methods that use an amidite compound, which is one species of the nucleoside derivative described.

As the oligonucleotide of the present teaching is provided with the nucleotide unit of the present teaching, is capable of selectively and stably hybridizing with RNA while at the same time is provided with base discrimination capability, allowing an RNA with a specific sequence to be detected. Moreover, as it per se has fluorescence capability, a gene mutation such as a single base polymorphism can also be detected.

In addition, since it hybridizes with an RNA highly selectivity, it can be used in particular for intracellular RNA detection, and real time detection of intracellular gene expression. In addition, solid phase supports such as chips, beads, and the like with these oligonucleotides retained thereon can be used as examination devices, diagnostic devices or a part thereof.

The oligonucleotide of the present teaching can adopt the morphologies of various gene expression control agents. That is to say, it can be used in an antigene, an antisense, an aptamer, an miRNA and a ribozyme. In addition, the oligonucleotide of the present teaching can also be used in an siRNA, an shRNA, an antisense, an ribozyme and an aptamer.

The oligonucleotide of the present teaching can be used in a probe and a primer. A probe is an oligonucleotide having, by design or by selection, a base sequence dictated specifically by the target nucleic acid, and acquired so as to hybridize with the target nucleic acid under a given stringency. From the foregoing, the oligonucleotide probe of the present teaching, in particular, can be used preferably for intracellular RNA detection, and particularly for real time detection.

Figure 9:
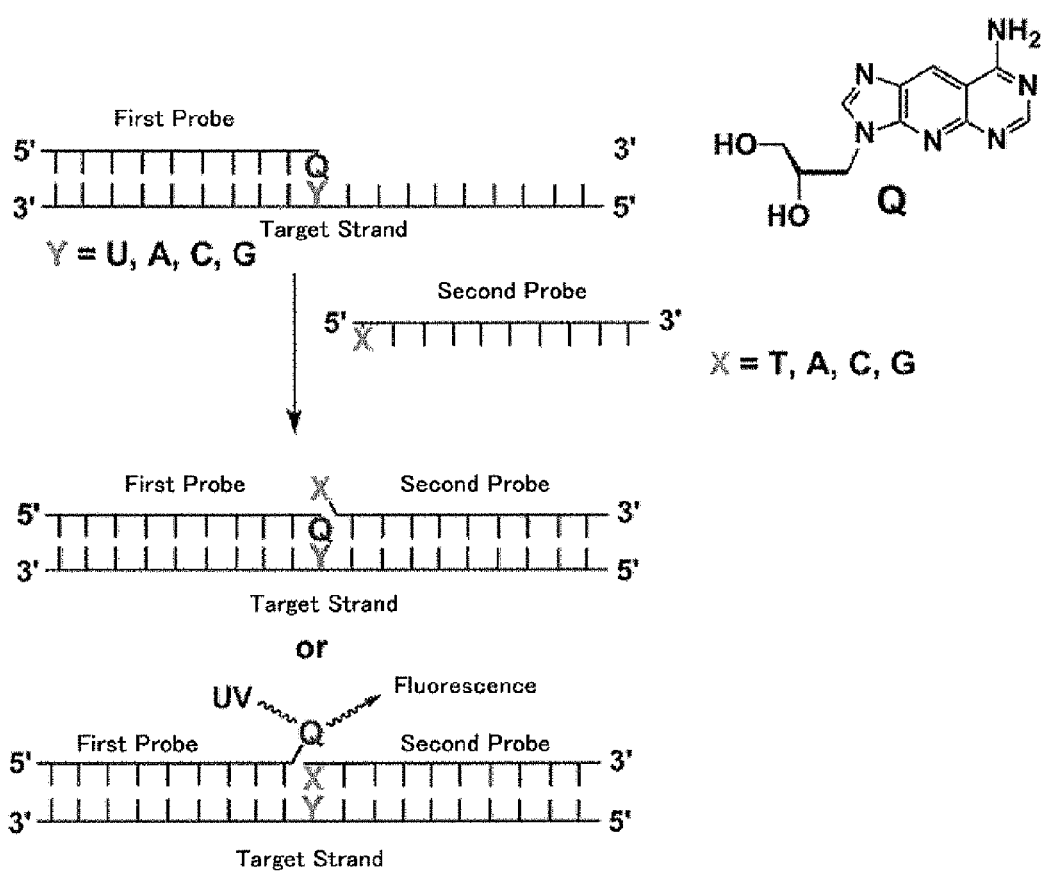
FIG. 9 shows one example of the probe set of the present teaching.

As the nucleotide derivative unit that the oligonucleotide of the present teaching contains per se emits fluorescence, a probe set using this for detecting a mutation on the RNA is provided. This probe set can be constituted from a first probe that has the nucleotide derivative unit of the present teaching and a second probe that does not have the nucleotide derivative unit of the present teaching. The first probe is arranged to be provided with the nucleotide derivative unit of the present teaching at a position corresponding to the mutation site. In addition, it is arranged to have such a nucleotide derivative unit at the 3' end or the 5' end of the probe. For instance, as shown in FIG. 9, when the first probe is to be hybridized on the 3' side of the target strand (RNA in the example shown in FIG. 9), its is arranged to have the nucleotide derivative unit of the present teaching at the 3' end. Note that the nucleotide derivative unit may be one that has a base analog corresponding to (complementing with) a base that has the possibility of being present at the mutation site to be detected, or may not be so. The first probe may be of one species or may be of two species or more. The species (number) of the first probe is determined according to the species of the nucleotide derivative unit of the present teaching provided at the position corresponding to the mutation site to be detected.

In addition, the second probe is arranged so as to provide a deoxynucleotide having a base corresponding to (complementing with) a base that has the possibility of being present at the mutation site to be detected. In addition, it is arranged to have this mutation-corresponding nucleotide at the 3' end or the 5' end of the probe. For instance, as shown in FIG. 9, when the second probe is to be hybridized on the 5' side of the target strand (RNA), it is arranged to have a suitable deoxynucleotide at the 5' end. The second probe may be of one species or may be of two species or more. The species (number) of the second probe is determined according to the species of the deoxynucleotide provided at the position corresponding to the mutation site to be detected.

By preparing, as described above, a probe having the nucleotide derivative unit of the present teaching at a position corresponding to the mutation site to be detected and a probe having a conventional deoxynucleotide unit complementary to a base that has the possibility of being present at the same mutation site, the base of the mutation site can be identified from the match/mismatch of the first probe and the match/mismatch of the second probe with respect to the mutation site. For instance, when the first probe and the second probe match with the mutation site, as the first probe and the second probe compete at the mutation site, at least a portion of the nucleotide units of the first probe flips out, allowing for fluorescence light emission. In addition, when the first probe is a mismatch and the second probe matches, the nucleotide unit of the first probe flips out widely from the duplex, allowing fluorescence to be emitted with higher intensity.

By preparing a plurality of the second probes so as to provide at the extremity corresponding to the mutation site all the bases that have the possibility of being present, the mutations for all the bases can be detected even if the first probe is of a single species. Such a probe set can be used preferably in particular for detecting a single base polymorphism.

Note that according to the present teaching, a detection method for a single base polymorphism using such a probe set is also provided. That is to say, there can be provided the step of preparing an RNA sample as a gene expression product having the possibility of containing a single base polymorphism, the step of bringing into contact in a hybridizable manner the first probe, the second probe and the RNA sample in all the combinations obtained by combining one species of the first probe and one species of the second probe selected from the probe set, and the step of detecting a fluorescence signal, based on the first probe, of the hybridization product between the RNA sample, the first probe and the second probe.

An RNA sample can prepare from various test entities by well known methods. As test entities, there is no particular limitation, such as various body fluids including blood and tissues.

There is not particular limitation on the form (order) of contact between the RNA sample, the first probe and the second probe. There may be a form in which the first probe and the second probe are brought simultaneously into contact with the RNA sample, or the second probe may be brought into contact after the first probe has been brought into contact. In addition, the first probe may be brought into contact after the second probe has been brought into contact.

The conditions for hybridization are determined suitably according to the species of the RNA sample and the probes. In addition, also in this detection method, an array with at least one portion among the first probe and the second probe immobilized on a solid phase support can be used.

The oligonucleotide of the present teaching can also be a probe of the molecular beacon type having a stem-loop structure. That is to say, it can also be a probe which base sequence has been designed to be able to form a stem and a loop. By providing the nucleotide unit of the present teaching in this loop, such a probe comprising being prone to fluorescent color emission by the base analog portion flipping out from the loop, emitting fluorescence when not non-hybridized and extinguishing itself when hybridized, can be constructed. According to such a probe, hybridization can be readily detected.

From the foregoing, the oligonucleotide of the present teaching can be used as a gene expression inhibitor by constructing it to function as an siRNA, antisense or the like. In addition, the oligonucleotide of the present teaching can be used as an active component of a medicinal composition for preventing and treating a disease in human and non-human animals. For instance, against a disease associated with gene expression, an oligonucleotide derivative of the present teaching constructed as a gene expression inhibitor is effective for preventing or treating such a disease.

In addition, the oligonucleotide of the present teaching can be used as a hybridization reagent (typically, an examination reagent, a diagnostic reagent or the like) such as a probe or a primer, by using the RNA-targeted hybridization function thereof. Owing to it hybridizing highly selectively with RNA, it can be preferably used for, in particular, intracellular RNA detection, real time detection of intracellular gene expression.

In addition, solid phase supports such as chips, beads, and the like with these oligonucleotides retained thereon can be used as examination devices, diagnostic devices or a part thereof. Furthermore, such an examination reagent and diagnostic drug can also be used as an examination or diagnostic kit combined with another reagent drug, diagnostic drug, device or the like.

The oligonucleotide of the present teaching can also be used in gene expression suppression methods in cells of human and non-human animals in the form of an inheritance expression regulation agent. In addition, the oligonucleotide of the present teaching can also be used in detection methods for specific genes or specific mutations in nucleic acid samples acquired from human and non-human animals, in the form of a hybridization reagent.

Hereafter, the present teaching will be described concretely by giving examples; however, these example are not to limit the present teaching.

Example 1

In the present example, a tricyclic nucleoside analog was synthesized by the following Scheme 3.

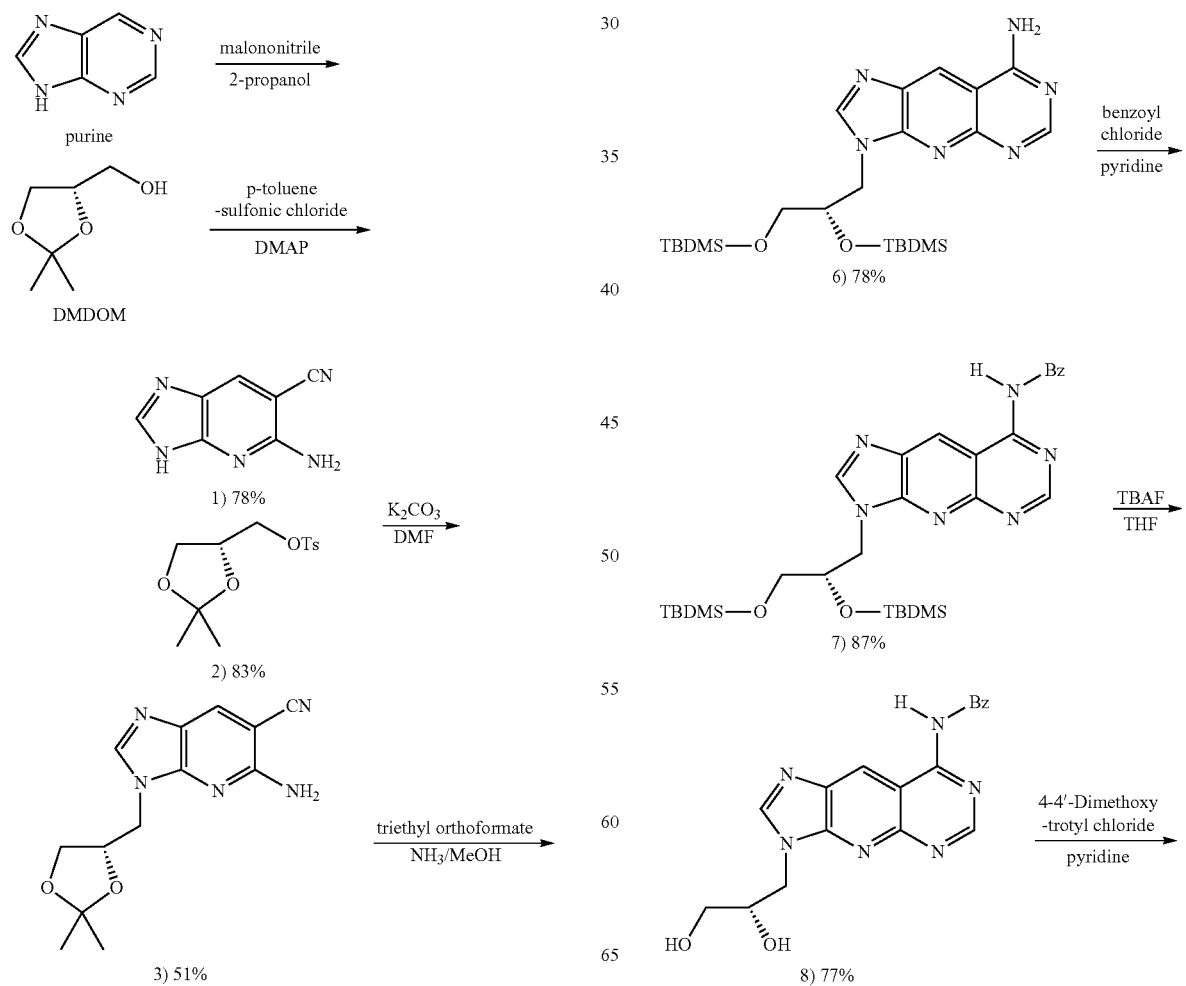

-continued

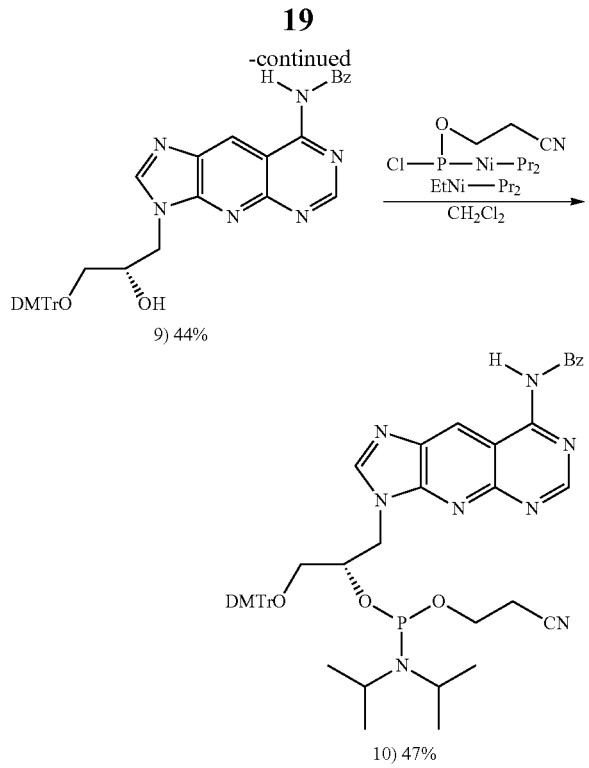

9) 44%

10) 47%

Note that the experimental conditions for obtaining each of the products (1) to (10) in the Scheme 3 were as follows:
Reagents and conditions: (1) Malononitrile, 2-propanol, 90° C., 78%. (2) p-toluenesulfonilchloride, DMAP, CH$_2$Cl, rt, 83%. (3) K$_2$CO$_3$, DMF, 60° C., 51%. (4) (i) triethyl orthoformate, 100° C., (ii) NH$_3$/MeOH, 110° C., 65%. (5) 80% CH$_3$COOH, 60° C. (6) TBDMS, Imidazole, DMF, 78%. (7) Benzoyl chloride, pyridine, 87%. (8) TBAF, THF, 77%. (9) 4-4'-Dimethoxytrityl chloride, pyridine, 44%. (10) i-Pr$_2$NP (Cl) OCE, Huning Base, CH$_2$Cl$_2$, rt, 47%.

(1) Synthesis of 5-Aminoimdazo[4,5-b]pyrimidine-6-carbonitrile

In 60 mL of 2-propanol, 1.0 g (8.3 mmol) of purine was dissolved, 2.6 g (39 mmol, 4.7 eq) of Malononitrile was added and stirred under argon atmosphere, maintaining 90° C. with an oil bath. (yellow, transparent) After stirring for 99 hours, the disappearance of the raw materials was checked by TLC and [the solution] was cooled to room temperature. (red wine color) After cooling to room temperature, since a crystalline object appeared in the solution, this crystal was filtered by aspiration while washing with 2-propanol cooled with ice water to obtain a crystalline object (1) (luminous green). The obtained crystal was dried overnight with a vacuum pump and an NMR measurement was carried out (yield: 1.5 g, 9.75 mmol; yield: 58%).
$^1$H NMR (400 MHz, DMSO) δ; 6.58 (2H, s, 6-CH and 8-CH), 8.17 (3H, s, 2-NH$_2$, 9-NH)

(2) Synthesis of 2,2-Dimethyl-4-(p-toluenesulfonyloxymethyl)-1,3-dioxolane

To 1.3 g, 1.2 ml (10 mmol) of Dimethyl-1,3-dioxolane-4-methanol, 3.7 g (3.0 mmol, 3.0 eq) of 4-Dimethyl amino pyridine dried for one hour was added and dissolved with 100 mL of CH$_2$Cl$_2$. Thereafter, 2.3 g (12 mmol, 1.2 eq) of p-Toluenesulfonyl chloride was added, then, [the solution] was stirred for the first 30 minutes dipped in cold water at room temperature under argon atmosphere (colorless transparent). After stirring for 18 hours, the disappearance of the raw materials was checked by TLC, liquid separation was carried out with a separating funnel (organic solvent: CDCl$_3$) and the oil layer was dried with anhydrous Na sulfate. An hour later, cotton plug-filtered and concentrated with an evaporator, [the solution] was the target compound was isolated by silica gel column chromatography (CHCl$_3$→CHCl$_3$:MeOH=100 to 10:1) to obtain an oily liquid (2) (pale yellow transparent to colorless transparent). The obtained liquid was dried overnight and an NMR measurement was carried out. (yield: 1.85 g, 8.3 mmol; yield 83%)
$^1$H NMR (400 MHz, CDCl$_3$) δ; 1.31 (3H, s, 2-CH$_3$), 1.34 (3H, d, 2-CH$_3$), 2.46 (3H, s, 4-phenylmethyl), 3.72-3.82 (1H, q, 4-sulfonylmethyl), 3.95-4.06 (3H, m, 4 sulfonylmethyl), 4.22-4.31 (1H, m, 4-CH), 7.27-7.37 (2H, d, 5-CH$_2$), 7.76-7.84 (2H, d, 4-1'-CH$_2$)

(3) Synthesis of 9-(4'-4'-dimethyl-3',5'-dioxolane-methyl)-1carbonitrile-2-aminopurine To 0.7 g (4.4 mmol) of 5-Aminoimdazo[4,5-b]pyrimidine-6-carbonitrile, 0.73 g (5.3 mmol, 1.2 eq) of K$_2$CO$_3$ was added and dried further for one hour. After drying, 1.17 g (5.3 mmol, 1.2 eq) of 2,2-Dimethyl-4-(p-toluene-sulfonyloxymethyl)-1,3-dioxolane was dissolved in 40 ml of DMF, and this solution was added to the earlier flask of 5-Aminoimdazo[4,5-b]pyrimidine-6-carbonitrile and K$_2$CO$_3$, and stirred under argon atmosphere while maintained to 60° C. with an oil bath. (light red)
After stirring for 70 hours, the disappearance of the raw materials was confirmed, liquid separation was carried out with a separating funnel (organic solvent: ethyl acetate), and the oil layer was dried with anhydrous Na sulfate. An hour later, cotton plug-filtered and concentrated with an evaporator, [the solution] was the target compound was isolated by silica gel column chromatography (CHCl$_3$→CHCl$_3$:MeOH=100:1) to obtain a white solid (3) (yield: 0.25 g, 0.92 mmol; yield: 21%).
$^1$HNMR (400 MHz, DMSO) δ; 1.33 (3H, s, 9-4'-CH$_3$), 1.38 (3H, s, 9-4'-CH$_3$) 1.61 (1H, s, 9-NH), 3.69-3.73 (2H, q, 9-6'-CH$_2$), 4.08-4.12 (2H, q, 9-6'-CH$_2$), 4.16-4.21 (2H, q, 9-1'-CH$_2$), 4.29-4.34 (2H, q, 9-1'-CH$_2$), 4.43-4.49 (1H, m, 9-2'-CH), 5.11 (2H, s, 2-NH$_2$), 7.97 (1H, s, 6-CH), 8.07 (1H, s, 8-CH)
HRMS (FAB) calcd for C$_{13}$H$_{15}$N$_5$O$_2$ (MH$^+$); 273.12258. Found; 273.12291

(4) Synthesis of 13-(4'-4'-dimethyl-3',5'-dioxolane-methyl)-6-aminoimidazo-quinazoline To 0.27 g (1.0 mmol) of 13-(4'-4'-dimethyl-3',5'-dioxolane-methyl)-6-aminoimidazo quinazoline, 8 mL of triethyl orthofomate was added and stirred while maintaining 100° C. with an oil bath (colorless transparent).
After stirring for 52 h, since the substance had started to break when confirmation of the disappearance of the raw materials by TLC was attempted, stirring was immediately stopped, the solvent was removed by reduced pressure and concentrated (dark yellow). The concentrate was dissolved in NH$_3$/MeOH, transferred to a 100 mL steel container and stirred while maintaining 110° C. with an oil bath. After stirring for 121 h, the disappearance of the raw materials was checked by TLC, and [the concentrate] was concentrated with a water-flowing evaporator. Dissolving the concentrated material in (CHCl$_3$:MeOH=5:1), adding silica, and concentrating with an evaporator, caused the substance to adsorb onto silica. After the adsorption, the target compound was isolated by silica gel column chromatography (CHCl$_3$:MeOH=15:1→10:1) to obtain a dark yellow solid (4). The obtained solid was dried overnight and an NMR measurement was carried out (yield: 0.15 g, 0.499 mmol; yield: 65.0%).

$^1$HNMR (400 MHz, DMSO) δ; 1.22 (3H, s, 12-4'-CH$_3$), 1.27 (3H, s, 12-4'-CH$_3$), 3.80-3.83 (2H, q, 12-1'-CH$_2$), 4.36-4.49 (2H, q, 12-6'-CH$_2$), 4.55-4.58 (1H, m, 12-2'-CH), 7.98 (2H, s, 2-NH$_2$), 8.47 (1H, s, 2-CH), 8.63 (1H, s, 7-CH), 9.03 (1H, s, 11-CH)

(5) Synthesis of 13-(2'-4'-hydroroxi)-6-aminoimidazo-quinazoline

To 0.3 g (1.0 mmol) of 13-(2'-4'-hydroxy)-6-aminoimidazo-quinazoline, 5 mL of 80% diluted acetic acid was added and stirred while maintaining 60° C. with an oil bath.

At 9 h after stirring was started, progression of the reaction was checked by TLC, then, acetic acid was removed by reduced pressure with a water-flowing evaporator to obtain a yellow solid (5). The obtained solid was dried overnight and an NMR measurement was carried out.

$^1$HNMR (400 MHz, DMSO) δ; 1.22 (1H, s, 13-2'-1"-OH), 1.27 (1H, s, 13-3'-1"-OH), 3.93 (2H, s, 13-1'-CH$_2$), 4.11-4.17 (2H, q, 13-1'-CH$_2$), 4.45-4.50 (2H, q, 12-3'-CH$_2$), 4.88 (2H, t, 12-3'-CH$_2$), 5.13-5.15 (1H, s, 13-2'-CH), 7.97 (2H, s, 6-NH$_2$), 8.47 (1H, s, 2-CH), 8.59 (1H, s, 7-CH), 9.01 (1H, s, 12-CH)

Elemental Anal. Calcd for C$_{11}$H$_{12}$N$_6$O$_2$.1/5H$_2$O: C, 50.29; H, 4.74; N, 30.87.

Found: C, 50.37; H, 4.87; N, 30.89.

(6) Synthesis of 13-(2'-1",4'-tert-butyldimethyl-silane)-6-aminoimidazo-quinazoline To 260 mg (1.0 mmol) of 13-(2'-1",4'-tert-butyldimethyl-silane)-6-aminoimidazo-quinazoline, 10 ml of DMF, 544 mg (8.0 mmol, 8.0 eq) of imidazole and 600 mg (4.0 mmol, 4.0 eq) of tert-butyldimethyl-chlorosilane were added and stirred under argon atmosphere at room temperature (dark yellow transparent). At 18 h after stirring was started, the disappearance of the target compound was checked by TLC, liquid separation was carried out with a separating funnel (organic solvent: ethyl acetate) (NaHCO$_3$×3→saturated sodium chloride water×1) and then dehydration was carried out for 1 h with anhydrous Na$_2$SO$_4$. After dehydration, concentration was carried out with an evaporator, the target compound was isolated by silica gel column chromatography (development solvent: CHCl$_3$:MeOH=20:1 to 10:1), the solvent was removed by reduced pressure with an evaporator to obtain a white solid (6). The obtained solid dried overnight with a vacuum pump and an NMR measurement was carried out (yield: 380 mg, 0.78 mmol; yield: 77.7%).

$^1$HNMR (400 MHz, DMSO) δ; −0.71 (3H, s, 13-3'-2"-CH$_3$), −0.23 (3H, s, 13-2'-2"-CH$_3$), −0.01 (6H, s, 13-2'-2", 3'-2"-2CH$_3$), 0.57 (9H, s, 13-3'-3"-3CH$_3$), 0.82 (9H, s, 13-2'-3"-3CH$_3$), 3.57 (2H, s, 13-1'-CH$_2$), 3.58 (2H, q, 13-1'-CH$_2$), 4.16 (2H, q, 12-3'-CH$_2$), 4.19 (2H, t, 12-3'-CH$_2$), 4.38-4.40 (1H, w, 13-2'-CH), 7.92 (2H, s, 6-NH$_2$), 8.39 (1H, s, 2-CH), 8.50 (1H, s, 7-CH) 8.93 (1H, s, 12-CH)

HRMS (FAB) calcd for C$_{23}$H$_{40}$N$_6$O$_2$Si$_2$ (MH$^+$); 488.27514. Found; 488.27596

(7) Synthesis of 13-(2'-1",4'-tert-butyldimethyl-silane)-6-aminoimidazo[1'-benzoyl]-quinazoline To 530 mg (1.1 mmol) of 13-(2'-1",4'-tert-butyldimethyl-silane)-6-aminoimidazo[1'-benzoyl]-quinazoline, pyridine 20 ml, benzoyl chloride 0.11 ml, 0.15 mg (1.1 mmol, 1.0 eq) were added and stirred under argon atmosphere at room temperature (yellow-green transparent).

At 2 h after stirring was started, from the TLC results, as benzoyl chloride tended to be lacking, 0.11 ml, 0.15 mg (1.1 mmol, 1.0 eq) was added. At 7 h after stirring was started, the disappearance of the target compound was checked by TLC, liquid separation was carried out with a separating funnel (organic solvent: CHCl$_3$) (NaHCO$_3$×2→saturated sodium chloride water×1) and then dehydration was carried out with anhydrous Na$_2$SO$_4$ for one hour. After dehydration, concentration was carried out with an evaporator, the target compound was isolated by silica gel column chromatography (development solvent: CHCl$_3$→CHCl$_3$:MeOH 10:1) and the solvent was removed by reduced pressure with an evaporator to obtain a light green solid (7). The obtained solid was dried overnight with a vacuum pump and an NMR measurement was carried out (yield: 557 mg, 0.94 mmol; yield: 87.0%).

$^1$HNMR (400 MHz, DMSO) δ; −0.46 (3H, s, 13-3'-2"-CH$_3$), −0.07 (3H, s, 13-2'-2"-CH$_3$), 0.09 (6H, s, 13-2'-2",3'-2"-2CH$_3$), 0.79 (9H, s, 13-3'-3"-3CH$_3$), 0.93 (9H, s, 13-2'-3"-3CH$_3$), 3.60-3.64 (2H, s, 13-1'-CH$_2$), 3.71-3.74 (2H, q, 13-1'-CH$_2$), 4.24-4.25 (2H, q, 12-3'-CH$_2$), 4.67-4.72 (2H, t, 12-3'-CH$_2$), 4.38-4.40 (1H, w, 13-2'-CH), 8.39-8.49 (3H, q, 6-1'-C$_6$H$_5$), 7.51 (1H, s, 2-CH), 7.55 (1H, s, 7-CH), 7.60 (1H, s, 12-CH), 9.60 (1H, s, 6-NH)

(8) Synthesis of 13-(2'-4'-hydroxy)-6-aminoimidazo[1'-benzoyl]-quinazoline

To 557 mg (0.94 mmol) of 13-(2'-4'-hydroxy)-6-aminoimidazo[1'-benzoyl]-quinazoline, 20 ml of THF, 3.4 g, 3.76 ml (3.76 mmol, 4.0 eq) of tetrabutylammonium fluoride, 1.0 M solution in tetrahydrofuran, were added and stirred under argon atmosphere at room temperature (yellow-green transparent). At 2 h after stirring was started, the disappearance of the target compound was checked by TLC, concentration was carried out with an evaporator, the target compound was isolated by silica gel column chromatography (development solvent: CHCl$_3$:MeOH=20:1 to 7:1) and the solvent was removed by reduced pressure with an evaporator to obtain a light green solid (8). The obtained solid was dried overnight with a vacuum pump and an NMR measurement was carried out (yield: 265 mg, 0.73 mmol; yield: 77.3%).

$^1$HNMR (400 MHz, DMSO) δ; 1.25 (1H, s, 13-2'-1"-OH), 1.26 (1H, s, 13-3'-1"-OH), 3.91 (2H, s, 13-1'-CH$_2$), 4.21-4.27 (2H, q, 13-1'-CH$_2$), 4.60-4.69 (2H, q, 12-3'-CH$_2$), 4.85-4.90 (2H, t, 12-3'-CH$_2$), 5.20-5.25 (1H, s, 13-2'-CH), 7.60-7.79 (3H, q, 6-1'-C$_6$H$_5$), 8.12 (1H, s, 2-CH), 8.60 (1H, s, 7-CH), 8.79 (1H, s, 12-CH), 9.42 (1H, s, 6-NH)

(9) Synthesis of 13-[2'-hydroxy-4'-(4,4'-dimethoxytrityl)]-6-aminoimidazo[1'-benzoyl]-quinazoline To 260 mg (0.71 mmol) of 13-(2'-4'-hydroxy)-6-aminoimidazo[1'-benzoyl]-quinazoline, 240 mg (0.71 mmol, 1.0 eq) of 4-4'-Dimethoxytrithyl chloride and 20 mL of pyridine were added and stirred under argon atmosphere at room temperature. At 2 h after stirring was started, from the TLC results, as 4-4'-Dimethoxytrithyl chloride tended to be lacking, 240 mg (0.71 mmol, 1.0 eq) was added. At 7 h after stirring was started, as it felt from the TLC that the reaction would not proceed further, liquid separation was carried out with a separating funnel (organic solvent: CHCl$_3$) (saturated NaHCO$_3$×2→saturated sodium chloride water×1) and then drying was carried out for 1 h with anhydrous sodium sulfate. After dehydration, concentration was carried out with an evaporator, the target compound was isolated by neutral silica gel column chromatography (development solvent: $CHCl_3$ to $CHCl_3$:MeOH=50:1) and the solvent was removed by reduced pressure with an evaporator to obtain a pale yellow compound (9) in a solid state (yield: 210 mg, 0.314 mmol; yield: 44.0%).

$^1$HNMR (400 MHz, $CDCl_3$, $D_2O$) δ; 1.25 (1H, s, 13-2'-1"-OH), 1.26 (1H, s, 13-3'-1"-OH), 3.91 (2H, s, 13-1'-$CH_2$), 4.21-4.27 (2H, q, 13-1'-$CH_2$), 4.60-4.69 (2H, q, 12-3'-$CH_2$), 4.85-4.90 (2H, t, 12-3'-$CH_2$), 5.20-5.25 (1H, s, 13-2'-CH), 7.60-7.79 (3H, q, 6-1'-$C_6H_5$), 8.12 (1H, s, 2-CH), 8.60 (1H, s, 7-CH), 8.79 (1H, s, 12-CH), 9.42 (1H, s, 6-NH)

(10) Synthesis of 13-[2'-[(N,N-diisopropylamino) phosphinyl]-4'-(4,4'-dimethoxytrityl)]-6-amino-imidazo[1'-benzoyl]-quinazoline After dissolving 135 mg (0.20 mmol) of 13-[2'-hydroxy-4'-(4,4'-dimethoxytrityl)]-6-aminoimidazo[1'-benzoyl]-quinazoline with 2 ml of CH2Cl2, 68 μL (0.40 mmol, 2.0 eq) of Huning Base, 67 μL (0.30 mmol, 1.5 eq) of i-$Pr_2NP(Cl)$ OCE were added and stirred under argon atmosphere at room temperature. After 30 minutes, the progression of the reaction was checked by TLC, and then stirring was stopped. Thereafter, liquid separation was carried out with a separating funnel (organic solvent: $CHCl_3$) (saturated $NaHCO_3$× 2→saturated sodium chloride water×1) and then dehydration treatment was carried out for several minutes with anhydrous sodium sulfate. After dehydration, concentration was carried out with an evaporator, the target compound was isolated by neutral silica gel column chromatography (development solvent: ethyl acetate) and the solvent was removed by reduced pressure with an evaporator to obtain a pale yellow compound (9) in a solid state. In addition, after drying target peak (149.1, 150.2 ppm) was checked by $^{31}$P NMR (yield: 122.1 mg, 0.314 mmol; yield: 47.0%).

Example 2

In the present example, oligonucleotides were synthesized using the amidite compounds synthesized in Example 1.

Using a DNA synthesizer, four species of oligonucleotides with the synthesized amidite compound of Compound 10 introduced in the X portions of the following sequences were synthesized and purified. In addition, among the following sequences, F-1 and F-2 have sequences directed to a molecular beacon-like stem-loop structure, the underlined portions of the sequence becoming stem portions and the non-underlined portions becoming loop portions.

F-1  5'-d(<u>TTC TGA</u> CTT X TTT <u>TCA GAA</u>)-3' (19 mar)

F-2  5'-d(<u>TTC TGA</u> CTA X ATT <u>TCA GAA</u>)-3' (19 mer)

F-3  5'-d(AAG GAA AX GAG GAA AGA)-3' (17 mer)

F-4  5'-d(AAG GAA XX GAG GAA AGA)-3' (17 mer)

Note that, after coupling by way of a synthesizer, the CPG was suspended in 1.2 ml of 28% $NH_4OH$ and incubated for 12 hours while maintained at 55° C. with an incubator. The CPG suspension was transferred to an eppendorf tube, further washed with twice 1 ml of a solution of $H_2O$:MeOH=3:1, and the solvent in the supernatant solution was eliminated by centrifuging in reduced pressure with a speedvac. After reducing pressure, this was recovered with 200 μL of loading solution to carry out electrophoresis and the target band was stirred together with the gel elution solution to elute the target oligonucleotide. The eluate was crudely purified using a Seppak C18 reverse phased column and the eluate thereof was eliminated by centrifuging in reduced pressure with a speedvac.

Quantification of the oligonucleotide was carried out using MALDI-TOF/MS. The results are shown in the following Table. From the results of TOF/MS F-1, 3 and 4 were determined as being the target oligonucleotides. The reason there are no measurement values for F-2 is because the OD value was an extremely small amount, and could not be detected.

Quantitative Values by MALDI/TPF

| No. | Sequence | observed | calculated |
|---|---|---|---|
| F-1 | 5'-d (<u>TTC TGA</u> CTT X TTT <u>TCA GAA</u>) -3' | 5779.9 | 5774.01 |
| F-2 | 5'-d (<u>TTC TGA</u> CTA X ATT <u>TCA GAA</u>) -3' | — | 5792.02 |
| F-3 | 5'-d (AAG GAA AX GAG GAA AGA) -3' | 5365.3 | 5365.01 |
| F-4 | 5'-d (AAG GAA XX GAG GAA AGA) -3' | 5380.6 | 5373.99 |

Example 3

Evaluation Temperature Stability for F-3 and F-4

$T_m$ Measurements

In the present example, the temperature stability of the duplexes between F-3 and F-4 and each of the complementary DNAs and RNAs was evaluated by way of the Tm values. Note that the concentrations of the respective strands in the $T_m$ measurements were, dissolved in 200 μL of measurement buffer solution (10 mM NaPhosphate (pH7.0)-100 mM NaCl) so as to obtain 3 μM, annealed at 95° C. for 3 minutes, then, left to stand for 1 h to be brought back to ordinary temperature, and 15-minute degassing was carried out. Of this sample, 150 μL was placed in a dedicated cell and measured. The sequences of F-3 and F-4 and the complementary DNA and RNA are shown in the following table.

| Oligonucletide | Sequence |
|---|---|
| F-3 | 5'-d (AAG-GAA-AQ-GAG-GAA-AGA)-3' |
| F-4 | 5'-d (AAG-GAA-QQ-GAG-GAA-AGA)-3' |
| Comlementary DNA | 3'-d (TTC-CTT-XX-CTC-CTT-TCT)-5' |

-continued

| Oligonucletide | Sequence |
|---|---|
| Comlementary RNA | 3'-r (UUC-CUU-XX-CUC-CUU-UCU)-5' |

* In the table, Q represents a tricyclic analog, XX in the complementary DNA represents TA, TT, TG and TC, and XX in the complementary RNA represents UA, UU, UG and UC.

Figure 10:
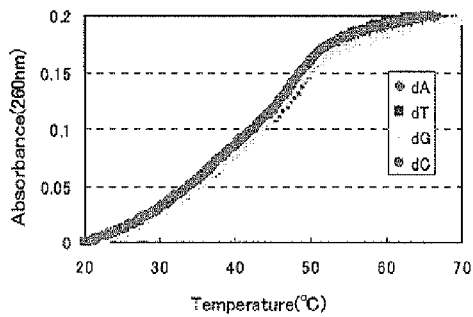
FIG. 10 shows the evaluation results of temperature stability of F-3 and F-4 in Example 3 (duplex with DNA).
Figure 10:
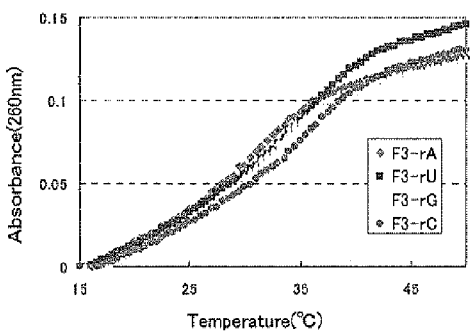
Figure 11:
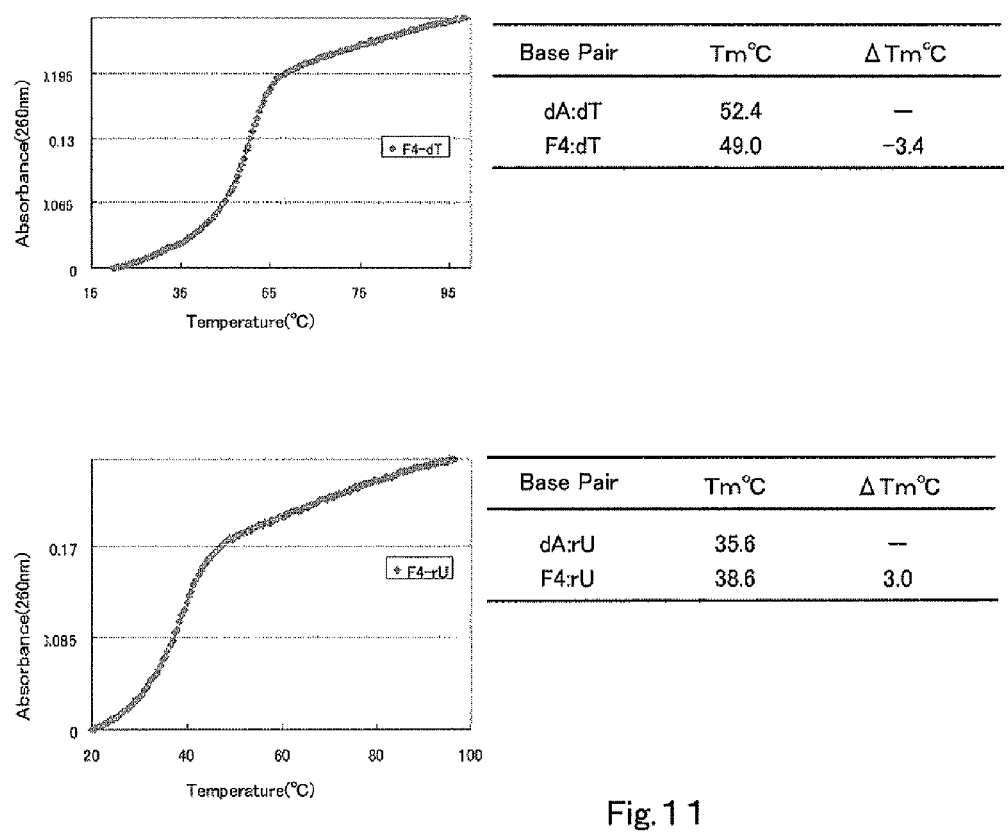
FIG. 11 shows the evaluation results of temperature stability of F-3 and F-4 in Example 3 (duplex with RNA).

As shown in FIG. 10 and FIG. 11, while all the probes destabilize significantly the duplexes with the DNA, in the cases where the RNA was complementary, on the contrary, the thermal stability of the duplexes were found to rise when the number of analogs increased.

Example 4

Evaluation of Temperature Stability of F-1

$T_m$ Measurement

In the present example, the temperature stability of the duplexes between F-1 and each of the complementary RNAs was evaluated by way of the Tm value. The concentrations of the respective strands in the $T_m$ measurements of F-1 were dissolved in 200 μL of measurement buffer solution (10 mM NaPhosphate (pH7.0)-100 mM NaCl) so as to obtain 3 μM, annealed at 95° C. for 3 minutes, then, left to stand for 1 h to be brought back to ordinary temperature, and 15-minute degassing was carried out.

The sequences of F-1 and complementary RNA thereto are indicated in the following table.

| Oligonucletide | Sequence | numbers of bases |
|---|---|---|
| F-1 | 5'-d (TTC-TGA-CTT-Q-TTT-TCA-GAA)-3' | 19 mer |
| Comlementary Strand | 5'-r (UUC-UGA-AAA-X-AAG-UCA-GAA)-3' | 19 mer |

* In the table, Q represents a tricyclic analog and X in the complementary RNA represents A, U, G or C. In addition, in the sequence of F-1, the sequence in the underlined portion indicates a stem site and the 5-mer in the center indicates a loop portion.

The thermal stabilities of F-1 and the complementary RNAs in two-stranded states were compared by measuring the 50% melting temperature $T_m$. The melting curves and the $T_m$ values are shown in FIG. 12.

Figure 12:
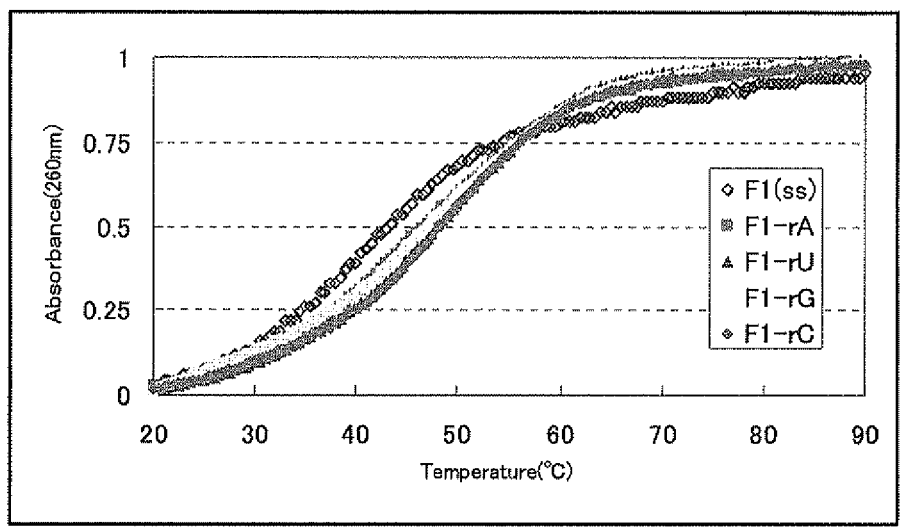
FIG. 12 shows the melting curves and the $T_m$ values when thermal stabilities of F-1 and complementary RNAs brought in double stranded states in Example 4 were compared by measuring the 50% melting temperature $T_m$.

As shown in FIG. 12, F-1 was found to present a thermal stability that was extremely satisfactory when forming a duplex with a complementary RNA, rather than when forming a duplex within the probe.

Example 5

Figure 13:
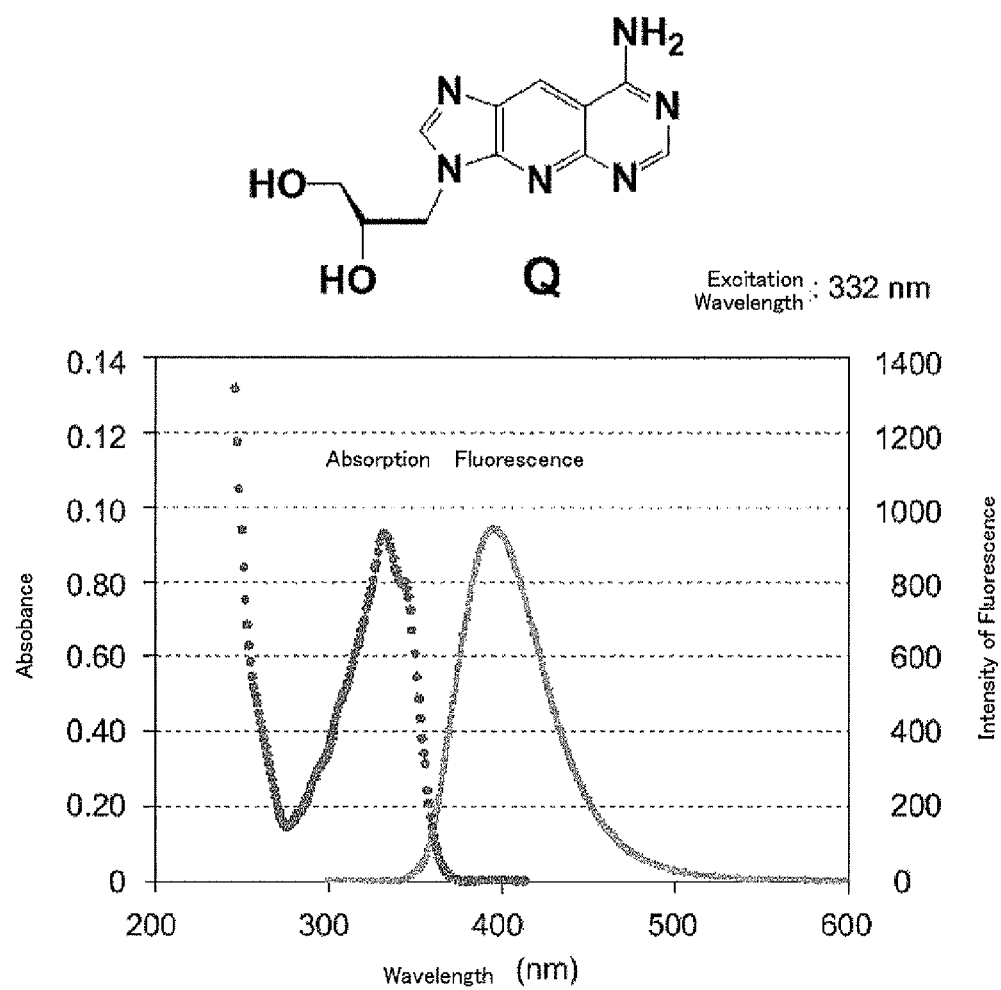
FIG. 13 shows the excitation wavelength and the fluorescence wavelength when a fluorescence measurement was performed with a fluorometer (Hitachi-F4500) in Example 5.
Figure 14:
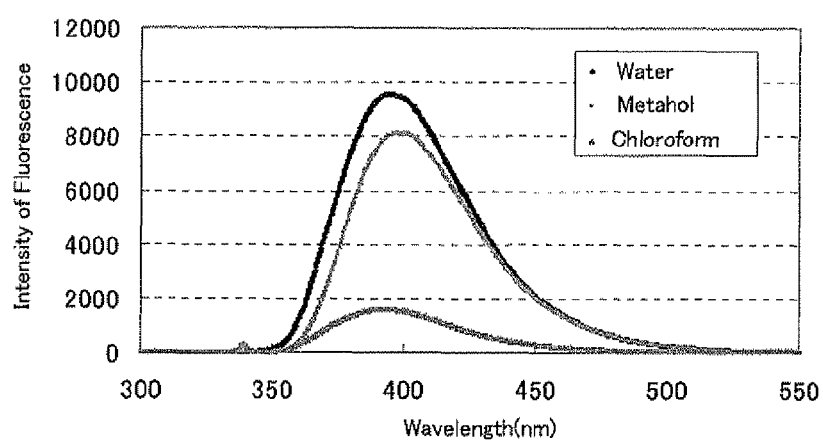
FIG. 14 shows each graph of fluorescence wavelength and fluorescence intensity when an excitation light ($\lambda_{ex}$=338 nm) was irradiated.

Measurements of the Fluorescence Characteristics and Polarity Dependency of the Tricyclic Analog In the present example, the fluorescence characteristics of the tricyclic analog were evaluated using the Compound 5 synthesized in Example 1. The Compound 5 was weighed out in the amount of 1 mg and dissolved in 500 μL of DMSO. After being thoroughly dissolved, 10 μL was transferred to a new eppendorf tube and 990 μL of distilled water was added. Thereafter, a fluorescence measurement was carried out with a fluorometer (Hitachi-F4500). The excitation and fluorescence wavelengths are shown in FIG. 13. In addition, the Compound (5) was weighed out in the amount of 1 mg, dissolved thoroughly in 500 μL of DMSO, then, 10 μL was transferred to each of three new eppendorf tubes, and 990 μL each of $H_2O$ (distilled water), dry MeOH and dry $CHCl_3$ were respectively added to prepare three species of samples. Each sample was transferred to a fluorescence cell vial and fluorescence measurement was carried out with a fluorometer (Hitachi-F4500). The respective graphs of fluorescence wavelength and fluorescence intensity when an excitation light ($\lambda_{ex}$=338 nm) was irradiated are shown in FIG. 14.

As shown in FIG. 13, the Compound 5 was found to absorb at approximately 338 nm and emit a fluorescence of approximately 400 nm. In addition, as shown in FIG. 14, it was revealed that the strongest fluorescence was emitted in distilled water, fluorescence was emitted also in methanol but no fluorescence was emitted in chloroform.

Example 6

Synthesis of Tricyclic Analog-Bonded CPG

In the present example, a 3-ring analog-bonded CPG unit (11) was prepared. That is to say, 143 mg (0.21 mmol) of the Compound (9) was dissolved in pyridine (2 mL), 0.5 μg (4.2 μMol, 0.02 eq) of DMAP and 63 mg (0.63 mmol, 3.0 eq) of succinic anhydride were added and stirred under Ar atmosphere at room temperature. After 110 hours, it was checked by TLC that there was no further progress in the reaction, and dilution with ethyl acetate, extraction/washing with water (×2), NaHCO3 (×1) and a saturated aqueous solution of NaCl (×1) and drying with sodium acetate were carried out to remove the solvent. From here, [what remains after the solvent was removed] was dissolved in DMF (4 mL), 0.62 g (0.047 mmol, 1.0 eq) of CPG was blended with the reaction solution and 36 mg (0.188 mmol, 4 eq) of WSC was added. [The solution] was shaken at room temperature for 2 days, thereafter, washed and dried with pyridine, then, 1.5 mL of acetic anhydride, 13.5 mL of pyridine and 0.183 g of DMAP [0.1 M DMAP in pyridine:$Ac_2O$ (9:1)] were added, and shaken at room temperature for 15 hours. The washing solution was changed in the Pyridine, MeOH and acetone order to wash and dry. As a result, the product was obtained with an activity of 31.2 μMol/g. Note that the activity was calculated by placing 6 mg of dried CPG resin on a glass filter, pouring a solution of $HClO_4$:EtOH=3:2, determining the optical density of the filtrate thereof at a wavelength of UV 498 nm (wavelength of the DMTr group), which was substituted in the following formula:

$$\frac{\text{Abs.}(498 \text{ nm}) \times \text{Vol.(solution)(mL)} \times 14.3}{\text{Weight (support)(mg)}} = \text{activity } (\mu \text{ mol/g})$$

Example 7

Oligonucleotides Having a Tricyclic Analog Integrated at an Extremity

Synthesis of FK-1 and FK-3

In the present example, a DNA synthesizer was used to synthesize and purify one species of oligonucleotide (FK-1) in which the synthesized CPG unite (11) (fluorescent analog Q) Claim was used for introduction at the X portion (3' end) of the following base sequence. In addition, an RNA and a DNA (having thymine instead of uracil as base) comprising the following target sequence were synthesized and purified. In addition, four species of oligonucleotides in which dA, dT, dG and dC had been introduced respectively at the N at the 5' end of the FK-2 sequence were also synthesized and purified. Note that the following target sequence (RNA) used in the present example contains 2677G/A/T, which is a gene polymorphism of the drug transporter MDR1 (P glycoprotein) (position 2677 corresponds to Y).

```
Target RNA:
5'-r(GAC-UCA-CCU-UCC-CAG-X-
-ACC-UUC-UAG-UUC-UUU)-3'  (31 mar)

FK-1:
5'-d(AAA-GAA-CTA-GAA-GGT-Q)-3'  (16 mar)

FK-2:
5'-d(Y-CTG-GGA-AGG-TGA-GTC)-3'  (16 mar)
```

Note regarding the use of the DNA synthesizer that purified oligonucleotides were acquired by operating similarly to Example 2.

Example 8

Hybridization of Two Species of Probes Against the Target Strand and Fluorescence Measurement

Part 1

The three species of oligonucleotide synthesized in Example 6, FK-1, FK-2 (four species with Y: dA, dT, dG or dC) and target RNA strand (X: rU) were dissolved in 1 mL of measurement buffer solution (10 mM Na Phosphate (pH7.0)-100 mM NaCl) so that the concentration of each strand was 3 µM, annealed at 95° C. for 3 minutes, then, left to stand for 1 h to be brought back to ordinary temperature, and 15-minute degassing was carried out. In addition to the total of four species of hybridization samples, a sample of FK1-alone was transferred to a fluorescence cell vial and a fluorescence measurement was carried out with a fluorometer (Hitachi-F4500). The respective graphs of fluorescence wavelength and fluorescence intensity when an excitation light ($\lambda_{ex}$=338 nm) was irradiated are shown in FIG. 15.

Figure 15:
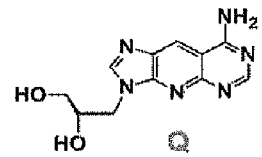
FIG. 15 shows each graph of fluorescence wavelength and fluorescence intensity when an excitation light ($\lambda_{ex}$=338 nm) was irradiated in Example 7.
Figure 15:
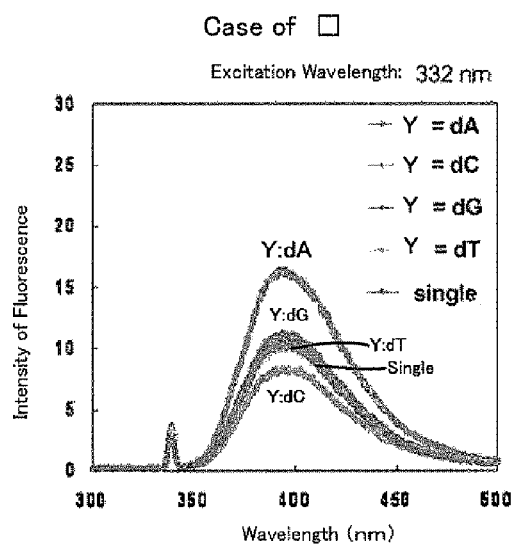

As shown in FIG. 15, the strongest fluorescence was displayed for the hybridization samples of FK-1 and FK-2 (Y: dA) which were respectively complementary to the X (rU) on the target strand, while it was approximately equivalent to approximately the FK-1 alone sample for the other hybridization samples. That is to say, it was thought that when FK-1 and FK-2 (Y: dA) were used as probes against the target strand, due to the competition between FK-1 and FK-2, as shown in FIG. 9, the fluorescent analog base Q flipped out from the duplex, emitting fluorescence. In addition, in the other hybridization samples, since each of the FK-2 probes was not a probe that competes with FK-1, the fluorescent base Q did not flip out from the duplex and thus did not exhibit fluorescence.

Example 9

Hybridization of Two Species of Probes Against the Target Strand and Fluorescence Measurement

Part 2

With FK-1, FK-2 (three species with Y: dA, dT or dC) and the target RNA strand (X: rU, rG, rA) synthesized in Example 6 in a given combination, the three species of oligonucleotides were dissolved in 1 mL of measurement buffer solution (10 mM Na Phosphate (pH7.0)-100 mM NaCl) so that the concentration of each strand was 3 µM, annealed at 95° C. for 3 minutes, then, left to stand for 1 h to be brought back to ordinary temperature, and 15-minute degassing was carried out. In addition to the total of four species of hybridization samples, a sample of FK1-alone was transferred to a fluorescence cell vial and a fluorescence measurement was carried out with a fluorometer (Hitachi-F4500). The respective graphs of fluorescence wavelength and fluorescence intensity when an excitation light ($\lambda_{ex}$=338 nm) was irradiated are shown in FIG. 16.

Figure 16:
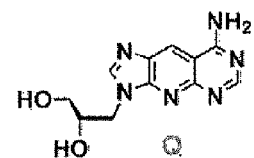
FIG. 16 shows each graph of fluorescence wavelength and fluorescence intensity when an excitation light ($\lambda_{ex}$=338 nm) was irradiated Example 8.
Figure 16:
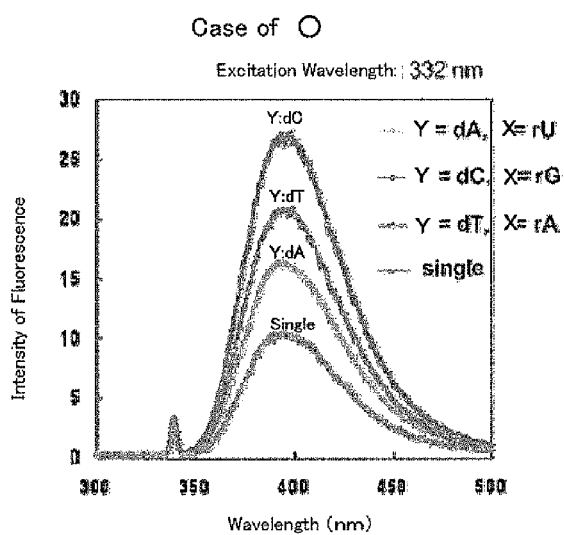

As shown in FIG. 16, when FK-1 and FK-2 (Y: dC) were hybridized against the target strand (X: rG), resulting from the target strand and FK-2 being strongly hybridized (GC base pair), the fluorescent base Q of FK-1 strongly flipped out and emitted the strongest fluorescence. Next, when FK-1 and FK-2 (Y: dT) were hybridized against the target strand (X: rA), resulting from the target strand and FK-2 being hybridized, the fluorescent base Q of FK-1 flipped out and emitted a strong fluorescence. In addition, regarding the hybridization sample of FK-1 and FK-2 (Y: dA) each of which being complementary to the X (rU) on the target strand, a fluorescence that was next to these was emitted.

From the foregoing, by hybridizing a probe (FK-2) with a normal base at a position corresponding to X in the target RNA (5' end) that is complementary to a base that has the possibility to be present as X and a probe (FK-1) provided with a fluorescent base Q at a position corresponding to X (3' end), fluorescence intensity is different according to the extent by which the fluorescent base Q flips out, this can be used to detect the base X in the target RNA.

[Sequence Listing Free Text]

SEQ ID NO. 1 to 7, 9,10: synthetic oligonucleotides
[Sequence Listing]

The invention claimed is:

1. An RNA hybridization reagent provided with one species or two or more species of nucleotide derivative units represented by any of the following Formulae (5) and (6):

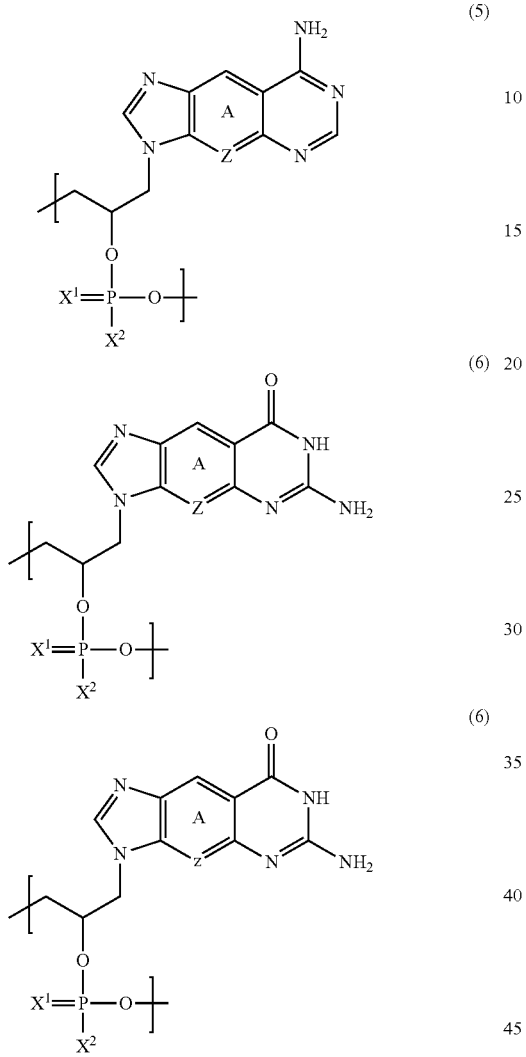

where Z represents a carbon atom or a nitrogen atom; $X^1$ represents O, S or Se; $X^2$ represents SH (or $S^-$), S or $Se^-$, or an alkyl group having 1 to 4 carbons or a morpholino group, wherein the RNA hybridization reagent selectively hybridizes RNA having a base sequence containing U corresponding to the Formula (5) and/or A corresponding to the Formula (6).

2. The RNA hybridization reagent according to claim 1, wherein the nucleotide derivative unit is represented by the Formula (5) and the Z is a nitrogen atom.

3. The RNA hybridization reagent according to claim 2, provided with the nucleotide derivative unit at an extremity.

4. The RNA hybridization reagent according to claim 1, having a base sequence which forms a stem-loop structure, and provided with the nucleotide derivative unit in the loop.

5. A probe set for detecting a mutation on an RNA, comprising:
a first probe provided with one species or two or more species of nucleotide derivative units represented by any of the following Formulae (5) and (6) at the 5' end or the 3' end corresponding to a site of the mutation; and
one species or two or more species of second probes provided with a deoxynucleotide having a base complementary to a base that has the possibility to be present in a site of the mutation at the 3' end or the 5' end corresponding to the site of the mutation:

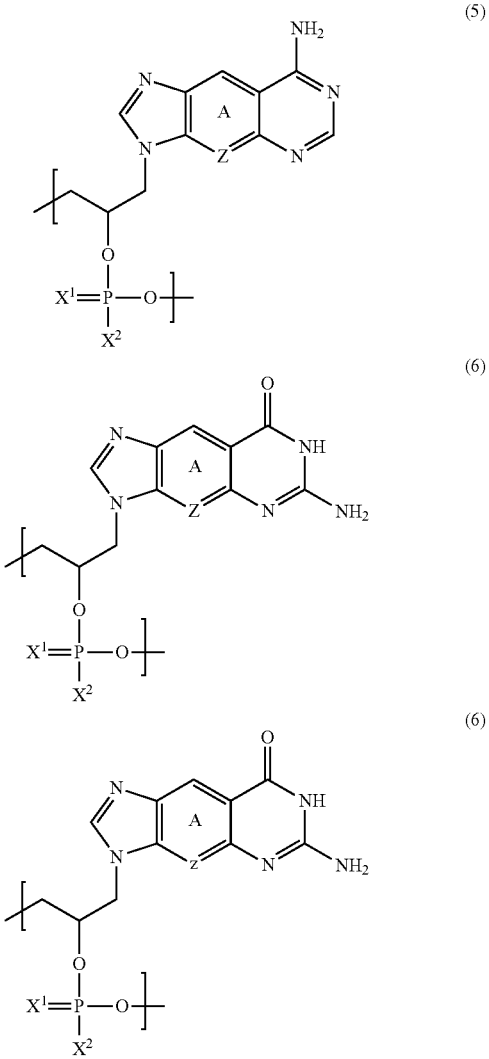

where Z represents a carbon atom or a nitrogen atom; $X^1$ represents O, S or Se; $X^2$ represents SH (or $S^-$), S or $Se^-$, or an alkyl group having 1 to 4 carbons or a morpholino group, wherein the first probe selectively hybridizes RNA having a base sequence containing U corresponding to the Formula (5) and/or A corresponding to the Formula (6).

6. A detecting method for a single base polymorphism, comprising:
preparing an RNA sample as a gene expression product having the possibility of containing the single base polymorphism;
with a probe set being provided containing a first probe provided with a nucleotide derivative unit represented by any of the following Formulae (5) and (6) at the 5' end or the 3' end corresponding to a site of the single base polymorphism, and one species or two or more species of second probes provided with a deoxynucleotide having a base complementary to a base that has the possibility to be present in a site of the single base polymorphism at the 3' end or the 5' end corresponding to the site of the single base polymorphism, causing the first probe, the second probe and the RNA sample to contact one another allowing hybridization in combinations of one species or two or more species obtained by combining one species of the first probe and one species of the second probe selected from the probe set,

[C16]

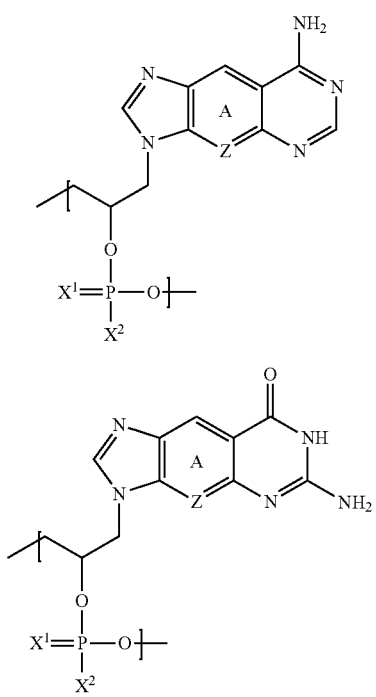

where Z represents a carbon atom or a nitrogen atom; X¹ represents O, S or Se; X² represents SH (or S⁻), S or Se⁻, or an alkyl group having 1 to 4 carbons or a morpholino group; and detecting a fluorescence signal based on the first probe which is a hybridization product among the RNA sample, the first probe and the second probe, wherein the first probe selectively hybridizes the RNA sample having a base sequence containing U corresponding to the Formula 5 and/or A corresponding to the Formula (6).

7. The RNA hybridization reagent according to claim 2, provided with the nucleotide derivative unit at an extremity.

8. The RNA hybridization reagent according to claim 2, having a base sequence which forms a stem-loop structure, and provided with the nucleotide derivative unit in the loop.

9. The RNA hybridization reagent according to claim 3, having a base sequence which forms a stem-loop structure, and provided with the nucleotide derivative unit in the loop.

10. The RNA hybridization reagent according to claim 7, having a base sequence which forms a stem-loop structure, and provided with the nucleotide derivative unit in the loop.

11. The RNA hybridization reagent according to claim 1, wherein the Z is a nitrogen atom.

12. The RNA hybridization reagent according to claim 1, wherein the RNA hybridization reagent has one or more deoxyribonucleotides with natural bases as one or more units other than the one species or two or more species of nucleotide derivative units represented by any of the formulae (5) and (6).

13. A method for forming a hybridized product with RNA comprising:

contacting the RNA hybridization reagent according to claim 1 with an RNA which has a base sequence containing U corresponding to the Formula (5) and/or A corresponding to the Formula (6).

14. The method according to claim 13, wherein the RNA hybridization reagent has one or more deoxyribonucleotides with natural bases as one or more units other than the one species or two or more species of nucleotide derivative units represented by any of the Formulae (5) and (6).

* * * * *